US011666526B2

(12) United States Patent
Deem et al.

(10) Patent No.: US 11,666,526 B2
(45) Date of Patent: *Jun. 6, 2023

(54) SYSTEMS AND METHODS FOR DELIVERY OF A THERAPEUTIC AGENT

(71) Applicant: The Foundry, LLC, Menlo Park, CA (US)

(72) Inventors: Mark E. Deem, Mountain View, CA (US); Hanson Gifford, Woodside, CA (US)

(73) Assignee: The Foundry, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/984,528

(22) Filed: Aug. 4, 2020

(65) Prior Publication Data
US 2020/0360677 A1 Nov. 19, 2020

Related U.S. Application Data

(60) Continuation of application No. 16/036,381, filed on Jul. 16, 2018, now Pat. No. 10,729,897, which is a continuation of application No. 15/358,187, filed on Nov. 22, 2016, now Pat. No. 10,022,529, which is a continuation of application No. 14/601,529, filed on Jan. 21, 2015, now Pat. No. 9,498,283, which is a continuation of application No. 13/660,629, filed on Oct. 25, 2012, now Pat. No. 8,961,391, which is a continuation of application No. 13/253,595, filed on Oct. 5, 2011, now Pat. No. 8,338,164, which is a continuation of application No. 12/559,278, filed on Sep. 14, 2009, now Pat. No. 8,133,497, which is a division of application No. 11/459,090, filed on Jul. 21, 2006, now Pat. No. 7,608,275.

(60) Provisional application No. 60/702,077, filed on Jul. 22, 2005.

(51) Int. Cl.
| | | |
|---|---|---|
| C12M 1/00 | (2006.01) | |
| A61K 9/00 | (2006.01) | |
| A61K 38/16 | (2006.01) | |
| A61K 38/48 | (2006.01) | |
| A61K 41/00 | (2020.01) | |
| A61N 1/32 | (2006.01) | |
| A61N 1/08 | (2006.01) | |
| A61N 1/30 | (2006.01) | |
| A61N 7/00 | (2006.01) | |
| A61B 18/14 | (2006.01) | |
| A61B 18/18 | (2006.01) | |
| A61N 5/10 | (2006.01) | |
| A61M 37/00 | (2006.01) | |
| A61B 18/00 | (2006.01) | |

(52) U.S. Cl.
CPC ........ *A61K 9/0021* (2013.01); *A61B 18/1492* (2013.01); *A61B 18/1815* (2013.01); *A61K 9/0078* (2013.01); *A61K 38/164* (2013.01); *A61K 38/168* (2013.01); *A61K 38/4893* (2013.01); *A61K 41/00* (2013.01); *A61K 41/0028* (2013.01); *A61K 41/0047* (2013.01); *A61M 37/00* (2013.01); *A61M 37/0092* (2013.01); *A61N 1/08* (2013.01); *A61N 1/303* (2013.01); *A61N 1/327* (2013.01); *A61N 5/10* (2013.01); *A61N 7/00* (2013.01); *C12Y 304/24069* (2013.01); *A61B 2018/0016* (2013.01); *A61B 2018/00214* (2013.01); *A61B 2018/00434* (2013.01); *A61B 2018/1861* (2013.01); *A61M 2210/1035* (2013.01); *A61N 2007/003* (2013.01); *Y02A 50/30* (2018.01)

(58) Field of Classification Search
CPC .................................................. A61K 9/0021
See application file for complete search history.

(56) References Cited

U.S. PATENT DOCUMENTS

| | | |
|---|---|---|
| 1,695,107 A | 12/1928 | Kahl |
| 3,918,449 A | 11/1975 | Pistor |
| 4,658,836 A | 4/1987 | Turner |
| 4,767,402 A | 8/1988 | Kost et al. |
| 4,976,710 A | 12/1990 | Mackin |

(Continued)

FOREIGN PATENT DOCUMENTS

| | | |
|---|---|---|
| CA | 2152002 A1 | 12/1995 |
| JP | 2002145784 A | 5/2002 |

(Continued)

OTHER PUBLICATIONS

Ahnert-Hilger., et al., "Inlroduction of Macromolecules into Bovine Adrenal-Medullary Chromaffin Cells and Rat Pheochromocytoma Cells (PC12) by Permeabilization with Streptolysin O: Inhibitory Effect of Teanus Toxin on Catecholamine Secretion," J. Neurochem, Jun. 1989, vol. 52 (6), pp. 1751-1758.

"Anonymous: Neurotoxin (from Wikipedia)," Retrieved from http://en.wikipedia.org/w/index.php?title=Neurotoxin&printable=yes, Apr. 2, 2015, 23 pages.

Application and File History for U.S. Appl. No. 11/459,090, filed Jul. 21, 2006, Inventors: Deem et al.

Application and File History for U.S. Appl. No. 12/559,278, filed Sep. 14, 2009, Inventors: Deem et al.

(Continued)

*Primary Examiner* — Albert M Navarro

(74) *Attorney, Agent, or Firm* — Patterson Thuente IP

(57) ABSTRACT

Methods and apparatus are provided for applying an fragment of a neurotoxin such as the active light chain (LC) of the botulinum toxin (BoNT), such as one of the serotype A, B, C, D, E, F or G botulinum toxins, via permeabilization of targeted cell membranes to enable translocation of the botulinum neurotoxin light chain (BoNT-LC) molecule across the targeted cell membrane to the cell cytosol where a therapeutic response is produced in a mammalian system. The methods and apparatus include use of catheter based delivery systems, non-invasive delivery systems, and transdermal delivery systems.

16 Claims, 14 Drawing Sheets

(56) References Cited

U.S. PATENT DOCUMENTS

| | | |
|---|---|---|
| 5,056,529 A | 10/1991 | De Groot |
| 5,139,029 A | 8/1992 | Fishman et al. |
| 5,158,536 A | 10/1992 | Sekins et al. |
| 5,286,254 A | 2/1994 | Shapland et al. |
| 5,304,120 A | 4/1994 | Crandell et al. |
| 5,331,947 A | 7/1994 | Shturman |
| 5,336,178 A | 8/1994 | Kaplan et al. |
| 5,409,483 A | 4/1995 | Campbell et al. |
| 5,432,092 A | 7/1995 | Bailey et al. |
| 5,496,304 A | 3/1996 | Chasan |
| 5,562,608 A | 10/1996 | Sekins et al. |
| 5,766,605 A | 6/1998 | Sanders et al. |
| 5,817,073 A | 10/1998 | Krespi |
| 5,820,589 A | 10/1998 | Torgerson et al. |
| 5,843,088 A | 12/1998 | Barra et al. |
| 5,860,974 A | 1/1999 | Abele |
| 5,902,268 A | 5/1999 | Saab |
| 5,957,961 A | 9/1999 | Maguire et al. |
| 5,964,223 A | 10/1999 | Baran |
| 5,972,026 A | 10/1999 | Laufer et al. |
| 6,033,397 A | 3/2000 | Laufer et al. |
| 6,056,744 A | 5/2000 | Edwards |
| 6,063,768 A | 5/2000 | First |
| 6,139,845 A | 10/2000 | Donovan |
| 6,200,333 B1 | 3/2001 | Laufer |
| 6,216,704 B1 | 4/2001 | Ingle et al. |
| 6,265,379 B1 | 7/2001 | Donovan |
| 6,283,989 B1 | 9/2001 | Laufer et al. |
| 6,299,633 B1 | 10/2001 | Laufer |
| 6,302,780 B1 | 10/2001 | Ahn et al. |
| 6,306,423 B1 | 10/2001 | Donovan et al. |
| 6,322,559 B1 | 11/2001 | Daulton et al. |
| 6,358,926 B2 | 3/2002 | Donovan |
| 6,361,554 B1 | 3/2002 | Brisken |
| 6,383,509 B1 | 5/2002 | Donovan et al. |
| 6,411,852 B1 | 6/2002 | Danek et al. |
| 6,425,887 B1 | 7/2002 | McGuckin et al. |
| 6,432,092 B2 | 8/2002 | Miller |
| 6,447,785 B1 | 9/2002 | Donovan |
| 6,448,231 B2 | 9/2002 | Graham |
| 6,464,680 B1 | 10/2002 | Brisken et al. |
| 6,475,160 B1 | 11/2002 | Sher |
| 6,488,673 B1 | 12/2002 | Laufer et al. |
| 6,506,399 B2 | 1/2003 | Donovan |
| 6,526,976 B1 | 3/2003 | Baran |
| 6,546,932 B1 | 4/2003 | Nahon et al. |
| 6,601,581 B1 | 8/2003 | Babaev |
| 6,620,415 B2 | 9/2003 | Donovan |
| 6,623,742 B2 | 9/2003 | Voet |
| 6,626,855 B1 | 9/2003 | Weng et al. |
| 6,632,440 B1 | 10/2003 | Quinn et al. |
| 6,634,363 B1 | 10/2003 | Danek et al. |
| 6,645,496 B2 | 11/2003 | Aoki et al. |
| 6,649,161 B1 | 11/2003 | Donovan |
| 6,658,279 B2 | 12/2003 | Swanson et al. |
| 6,719,694 B2 | 4/2004 | Weng et al. |
| 6,740,321 B1 | 5/2004 | Donovan |
| 6,767,544 B2 | 7/2004 | Brooks et al. |
| 6,770,070 B1 | 8/2004 | Balbierz |
| 6,773,711 B2 | 8/2004 | Voet et al. |
| 6,776,991 B2 | 8/2004 | Naumann |
| 6,827,931 B1 | 12/2004 | Donovan |
| 6,838,434 B2 | 1/2005 | Voet |
| 6,841,156 B2 | 1/2005 | Aoki et al. |
| 6,843,998 B1 | 1/2005 | Steward et al. |
| 6,846,312 B2 | 1/2005 | Edwards et al. |
| 6,847,849 B2 | 1/2005 | Mamo et al. |
| 6,861,058 B2 | 3/2005 | Aoki et al. |
| 6,872,397 B2 | 3/2005 | Aoki et al. |
| 6,917,834 B2 | 7/2005 | Koblish et al. |
| 6,974,578 B1 | 12/2005 | Aoki et al. |
| 7,027,869 B2 | 4/2006 | Danek et al. |
| 7,184,811 B2 | 2/2007 | Phan et al. |
| 7,371,231 B2 | 5/2008 | Rioux et al. |
| 7,462,179 B2 | 12/2008 | Edwards et al. |
| 7,608,275 B2 | 10/2009 | Deem et al. |
| 7,628,789 B2 | 12/2009 | Soltesz et al. |
| 7,747,324 B2 | 6/2010 | Errico et al. |
| 7,853,331 B2 | 12/2010 | Kaplan et al. |
| 8,007,495 B2 | 8/2011 | McDaniel et al. |
| 8,088,127 B2 | 1/2012 | Mayse et al. |
| 8,105,817 B2 | 1/2012 | Deem et al. |
| 8,133,497 B2 | 3/2012 | Deem et al. |
| 8,172,827 B2 | 5/2012 | Deem et al. |
| 8,226,638 B2 | 7/2012 | Mayse et al. |
| 8,338,164 B2 | 12/2012 | Deem et al. |
| 8,483,831 B1 | 7/2013 | Hlavka et al. |
| 8,489,192 B1 | 7/2013 | Hlavka et al. |
| 8,660,647 B2 | 2/2014 | Parnis et al. |
| 8,731,672 B2 | 5/2014 | Hlavka et al. |
| 8,740,895 B2 | 6/2014 | Mayse et al. |
| 8,777,943 B2 | 7/2014 | Mayse et al. |
| 8,808,280 B2 | 8/2014 | Mayse et al. |
| 8,821,489 B2 | 9/2014 | Mayse et al. |
| 8,911,439 B2 | 12/2014 | Mayse et al. |
| 8,932,289 B2 | 1/2015 | Mayse et al. |
| 8,961,391 B2 | 2/2015 | Deem et al. |
| 8,961,507 B2 | 2/2015 | Mayse et al. |
| 8,961,508 B2 | 2/2015 | Mayse et al. |
| 9,005,195 B2 | 4/2015 | Mayse et al. |
| 9,017,324 B2 | 4/2015 | Mayse et al. |
| 9,125,643 B2 | 9/2015 | Hlavka et al. |
| 9,149,328 B2 | 10/2015 | Dimmer et al. |
| 9,339,618 B2 | 5/2016 | Deem et al. |
| 9,398,933 B2 | 7/2016 | Mayse |
| 9,498,283 B2 | 11/2016 | Deem et al. |
| 9,539,048 B2 | 1/2017 | Hlvaka et al. |
| 10,022,529 B2 | 7/2018 | Deem et al. |
| 10,149,714 B2 | 12/2018 | Mayse et al. |
| 10,201,386 B2 | 2/2019 | Mayse et al. |
| 10,206,735 B2 | 2/2019 | Kaveckis et al. |
| 10,252,057 B2 | 4/2019 | Hlvaka et al. |
| 10,363,091 B2 | 7/2019 | Dimmer et al. |
| 10,368,937 B2 | 8/2019 | Kaveckis et al. |
| 10,575,893 B2 | 3/2020 | Mayse |
| 10,610,283 B2 | 4/2020 | Mayse et al. |
| 10,610,675 B2 | 4/2020 | Deem et al. |
| 10,729,897 B2 | 8/2020 | Deem et al. |
| 10,869,997 B2 | 12/2020 | Mayse |
| 10,894,011 B2 | 1/2021 | Deem et al. |
| 2001/0044596 A1 | 11/2001 | Jaafar |
| 2002/0013581 A1 | 1/2002 | Edwards et al. |
| 2002/0082197 A1 | 6/2002 | Aoki et al. |
| 2002/0087208 A1 | 7/2002 | Koblish et al. |
| 2002/0111620 A1 | 8/2002 | Cooper et al. |
| 2002/0143302 A1 | 10/2002 | Hinchliffe et al. |
| 2002/0198512 A1 | 12/2002 | Seward |
| 2003/0018344 A1 | 1/2003 | Kaji et al. |
| 2003/0023287 A1 | 1/2003 | Edwards et al. |
| 2003/0036755 A1 | 2/2003 | Ginn |
| 2003/0050591 A1 | 3/2003 | Patrick McHale |
| 2003/0118327 A1 | 6/2003 | Um et al. |
| 2003/0159700 A1 | 8/2003 | Laufer et al. |
| 2003/0202990 A1 | 10/2003 | Donovan et al. |
| 2003/0211121 A1 | 11/2003 | Donovan |
| 2003/0233099 A1 | 12/2003 | Danaek et al. |
| 2004/0009180 A1 | 1/2004 | Donovan |
| 2004/0010290 A1 | 1/2004 | Schroeppel et al. |
| 2004/0028676 A1 | 2/2004 | Klein et al. |
| 2004/0086531 A1 | 5/2004 | Barron |
| 2004/0091880 A1 | 5/2004 | Wiebusch et al. |
| 2004/0142005 A1 | 7/2004 | Brooks et al. |
| 2004/0151741 A1 | 8/2004 | Borodic |
| 2004/0175399 A1 | 9/2004 | Schiffman |
| 2004/0186435 A1 | 9/2004 | Seward |
| 2004/0213813 A1 | 10/2004 | Ackerman |
| 2004/0213814 A1 | 10/2004 | Ackerman |
| 2004/0220562 A1 | 11/2004 | Garabedian et al. |
| 2004/0226556 A1 | 11/2004 | Deem et al. |
| 2004/0248188 A1 | 12/2004 | Sanders |
| 2004/0253274 A1 | 12/2004 | Voet |
| 2005/0019346 A1 | 1/2005 | Boulis |
| 2005/0065575 A1 | 3/2005 | Dobak |
| 2005/0074461 A1 | 4/2005 | Donovan |

(56) References Cited

U.S. PATENT DOCUMENTS

| | | |
|---|---|---|
| 2005/0107853 A1 | 5/2005 | Krespi et al. |
| 2005/0152924 A1 | 7/2005 | Voet |
| 2005/0182393 A1 | 8/2005 | Abboud et al. |
| 2005/0183732 A1 | 8/2005 | Edwards |
| 2005/0240147 A1 | 10/2005 | Makower et al. |
| 2005/0245926 A1 | 11/2005 | Edwards et al. |
| 2006/0084966 A1 | 4/2006 | Maguire et al. |
| 2006/0106361 A1 | 5/2006 | Muni et al. |
| 2006/0153876 A1 | 7/2006 | Sanders |
| 2006/0222667 A1 | 10/2006 | Deem et al. |
| 2006/0225742 A1 | 10/2006 | Deem et al. |
| 2006/0254600 A1 | 11/2006 | Danek et al. |
| 2007/0021803 A1 | 1/2007 | Deem et al. |
| 2007/0025919 A1 | 2/2007 | Deem et al. |
| 2007/0043350 A1 | 2/2007 | Soltesz et al. |
| 2007/0083194 A1 | 4/2007 | Kunis et al. |
| 2007/0100390 A1 | 5/2007 | Danaek et al. |
| 2007/0106292 A1 | 5/2007 | Kaplan et al. |
| 2007/0118184 A1 | 5/2007 | Danek et al. |
| 2007/0129720 A1 | 6/2007 | Demarais et al. |
| 2007/0156185 A1 | 7/2007 | Swanson et al. |
| 2007/0250050 A1 | 10/2007 | Lafontaine |
| 2007/0267011 A1 | 11/2007 | Deem et al. |
| 2007/0270794 A1 | 11/2007 | Anderson et al. |
| 2008/0021369 A1 | 1/2008 | Deem et al. |
| 2008/0051839 A1 | 2/2008 | Libbus et al. |
| 2008/0091379 A1 | 4/2008 | Lynch et al. |
| 2008/0161890 A1 | 7/2008 | Lafontaine |
| 2008/0255642 A1 | 10/2008 | Zarins et al. |
| 2008/0312725 A1 | 12/2008 | Penner |
| 2009/0018538 A1 | 1/2009 | Webster et al. |
| 2009/0043301 A1 | 2/2009 | Jarrard et al. |
| 2009/0177192 A1 | 7/2009 | Rioux et al. |
| 2009/0221997 A1 | 9/2009 | Arnold et al. |
| 2010/0003282 A1 | 1/2010 | Deem et al. |
| 2010/0087775 A1 | 4/2010 | Deem et al. |
| 2011/0118725 A1 | 5/2011 | Mayse et al. |
| 2011/0152855 A1 | 6/2011 | Mayse et al. |
| 2011/0178569 A1 | 7/2011 | Parnis et al. |
| 2011/0257647 A1 | 10/2011 | Mayse et al. |
| 2011/0301587 A1 | 12/2011 | Deem et al. |
| 2012/0016363 A1 | 1/2012 | Mayse et al. |
| 2012/0016364 A1 | 1/2012 | Mayse et al. |
| 2012/0029261 A1 | 2/2012 | Deem et al. |
| 2012/0158101 A1 | 6/2012 | Stone et al. |
| 2012/0203216 A1 | 8/2012 | Mayse et al. |
| 2012/0203222 A1 | 8/2012 | Mayse et al. |
| 2012/0209261 A1 | 8/2012 | Mayse et al. |
| 2012/0209296 A1 | 8/2012 | Mayse et al. |
| 2012/0221087 A1 | 8/2012 | Parnis et al. |
| 2012/0302909 A1 | 11/2012 | Mayse et al. |
| 2012/0310233 A1 | 12/2012 | Dimmer et al. |
| 2012/0316552 A1 | 12/2012 | Mayse et al. |
| 2012/0316559 A1 | 12/2012 | Mayse et al. |
| 2013/0123751 A1 | 5/2013 | Deem et al. |
| 2013/0289555 A1 | 10/2013 | Mayse et al. |
| 2013/0289556 A1 | 10/2013 | Mayse et al. |
| 2013/0303948 A1 | 11/2013 | Deem et al. |
| 2013/0310822 A1 | 11/2013 | Mayse et al. |
| 2014/0186341 A1 | 7/2014 | Mayse |
| 2014/0257271 A1 | 9/2014 | Mayse et al. |
| 2014/0276792 A1 | 9/2014 | Kaveckis et al. |
| 2014/0371809 A1 | 12/2014 | Parnis et al. |
| 2015/0051597 A1 | 2/2015 | Mayse et al. |
| 2015/0141985 A1 | 5/2015 | Mayse et al. |
| 2015/0190193 A1 | 7/2015 | Mayse et al. |
| 2015/0366603 A1 | 12/2015 | Hlvaka et al. |
| 2016/0022351 A1 | 1/2016 | Kaveckis et al. |
| 2016/0038725 A1 | 2/2016 | Mayse et al. |
| 2016/0220851 A1 | 8/2016 | Mayse et al. |
| 2016/0310210 A1 | 10/2016 | Harshman et al. |
| 2017/0014571 A1 | 1/2017 | Deem et al. |
| 2018/0028748 A1 | 2/2018 | Deem et al. |
| 2018/0199993 A1 | 7/2018 | Mayse et al. |
| 2019/0105102 A1 | 4/2019 | Mayse et al. |
| 2019/0142510 A1 | 5/2019 | Mayse et al. |
| 2019/0142511 A1 | 5/2019 | Wahr et al. |
| 2019/0151018 A1 | 5/2019 | Mayse et al. |
| 2020/0001081 A1 | 1/2020 | Hlvaka et al. |
| 2020/0060750 A1 | 2/2020 | Kaveckis et al. |
| 2020/0085495 A1 | 3/2020 | Dimmer et al. |
| 2020/0222114 A1 | 7/2020 | Johnson et al. |
| 2020/0268436 A1 | 8/2020 | Mayse |

FOREIGN PATENT DOCUMENTS

| | | |
|---|---|---|
| WO | WO-9519805 A1 | 7/1995 |
| WO | WO-9934831 A1 | 7/1999 |
| WO | WO-0062699 A2 | 10/2000 |
| WO | WO-2004006954 A2 | 1/2004 |
| WO | WO-2004101028 A2 | 11/2004 |
| WO | WO-2005032646 A2 | 4/2005 |
| WO | WO-2005048988 A1 | 6/2005 |
| WO | WO-2004101028 A3 | 12/2006 |

OTHER PUBLICATIONS

Application and File History for U.S. Appl. No. 13/253,595, filed Oct. 5, 2011, Inventors: Deem et al.

Application and File History for U.S. Appl. No. 13/660,629, filed Oct. 25, 2012, Inventors: Deem et al.

Application and File history for U.S. Appl. No. 14/601,529, filed Jan. 21, 2015, Inventors: Deem et al.

Application and File History for U.S. Appl. No. 15/358,187, filed Nov. 22, 2016, Inventors: Deem et al.

Application and File History for U.S. Appl. No. 16/036,381, filed Jul. 16, 2018, Inventors: Deem et al.

Bigalke., et al., "Clostridial Neurotoxins," Handbook of Experimental Pharmacology (Aktories, K., and Just, I., eds), 2000, vol. 145, pp. 407-443.

Bittner., et al., "Isolated Light Chains of Botulinum Neurotoxins Inhibit Exocytosis," The Journal of Biological Chemistry, 1989, vol. 264(18), pp. 10354-10360.

Blindt., et al., "Development of a New Biodegradable Intravascular Polymer Stent with Simultaneous Incorporation of Bioactive Substances," The International Journal of Artificial Organs, 1999, vol. 22 (12), pp. 843-853.

Buzzi., "Diphtheria Toxin Treatment of Human Advanced Cancer," Cancer Research, 1982, vol. 42, pp. 2054-2058.

Chaddock., et al., "Expression and Purification of Catalytically Active, Non-Toxic Endopeptidase Derivatives of Clostridium Botulinum Toxin Type A," Protein Expression and Purification, Jul. 2002, vol. 25 (2), pp. 219-228.

Chang., "Cell Poration and Cell Fusion Using an Oscillating Electric Field," Biophys. J, 1989, vol. 56 (4), pp. 641-652.

De Paiva., et al., "Light Chain of Botulinum Neurotoxin is Active in Mammalian Motor Nerve Terminals When Delivered Via Liposomes," FEBS Lett, Dec. 1990, vol. 17:277(1-2), pp. 171-174.

European Search Report for Application No. EP06788062, dated Jan. 7, 2014, 9 pages.

Guzman., et al., "Bioeffects Caused by Changes in Acoustic Cavitation Bubble Density and Cell Concentration: A Unified Explanation Based on Cell-to-Bubble Ratio and Blast Radius," Ultrasound in medicine & biology, 2003, vol. 29 (8), pp. 1211-1222.

Guzman H.R, et al., "Equilibrium Loading of Cells with Macromolecules by Ultrasound: Effects of Molecular Size and Acoustic Energy," J PharmSci., Jul. 2002, vol. 91 (7), pp. 1693-1701.

International Preliminary Report on Patentability for Application No. PCT/US2006/028310, dated Jan. 22, 2008, 7 pages.

International Search Report and Written Opinion for Application No. PCT/US2006/028310, dated Aug. 8, 2007, 7 pages.

Kistner., et al., "Reductive Cleavage of Tetanus Toxin and Botulinum Neurotoxin A by the Thioredoxin System from Brain," Naunyn-Schmiedebergs Arch Pharmacal, Feb. 1992, vol. 345 (2), pp. 227-234.

Korpela., et al., "Comparison of Tissue Reactions in the Tracheal Mucosa Surrounding a Bioabsorbable and Silicone Airway Stents," Annals of Thoracic Surgery, 1998, vol. 66, pp. 1772-1776.

(56) References Cited

OTHER PUBLICATIONS

Kreitman., "Taming Ricin Toxin," Nature Biotechnology, 2003, vol. 21, pp. 372-374.
Office Action dated May 24, 2016 for Japanese Application No. JP2015-120827 filed Jun. 16, 2015, 7 pages.
Office Action dated Aug. 21, 2017 for Japanese Application No. 2016- 227703 filed Nov. 24, 2016, 4 pages.
Raj., "Editorial," Pain Practice, 2004, vol. 4 (1S), pp. S1-S3.
Schmitt G.S., et al., "Indwelling Transbronchial Catheter Drainage of Pulmonary Abscess," Ann Thorac Surg, Jan. 1988, vol. 45 (1), pp. 43-47.
Shaari., et al., "Rhinorrhea is Decreased in Dogs After Nasal Application of Botulinum Toxin," Otolaryngol Head Neck Surgery, Apr. 1995, vol. 112 (4), pp. 566-571.
Simpson., et al., "Isolation and Characterization of the botulinum Neurotoxins," Methods Enzymol, 1988, vol. 165, pp. 76-85.
Simpson L.L., "The Origin, Structure, and Pharmacological Activity of Botulinum Toxin," Pharmacol Reviews, Sep. 1981, vol. 33 (3), pp. 155-188.
Sundaram, et al., "An Experimental and Theoretical Analysis of Ultrasound-Induced Permeabilization of Cell Membranes," Biophysical Journal, May 2003, vol. 84 (5), pp. 3087-3101.
Tsuji., et al., "Biodegradable Stents as a Platform to Drug Loading," International Journal of Cardiovascular Interventions, 2003, vol. 5(1), pp. 13-16.
Unal., et al., "Effect of Botulinum Toxin Type A on Nasal Symptoms in Patients with Allergic Rhinitis: A Double-blind, Placebo-conlrolled Clinical Trial," Acta Oto-Laryngologica, Dec. 2003, vol. 123 (9), pp. 1060-1063.
Weaver, "Electroporation: A General Phenomenon for Manipulating Cells and Tissues," Journal of Cellular Biochemistry, Apr. 1993, vol. 51(4), pp. 426-435.

FIG. 1

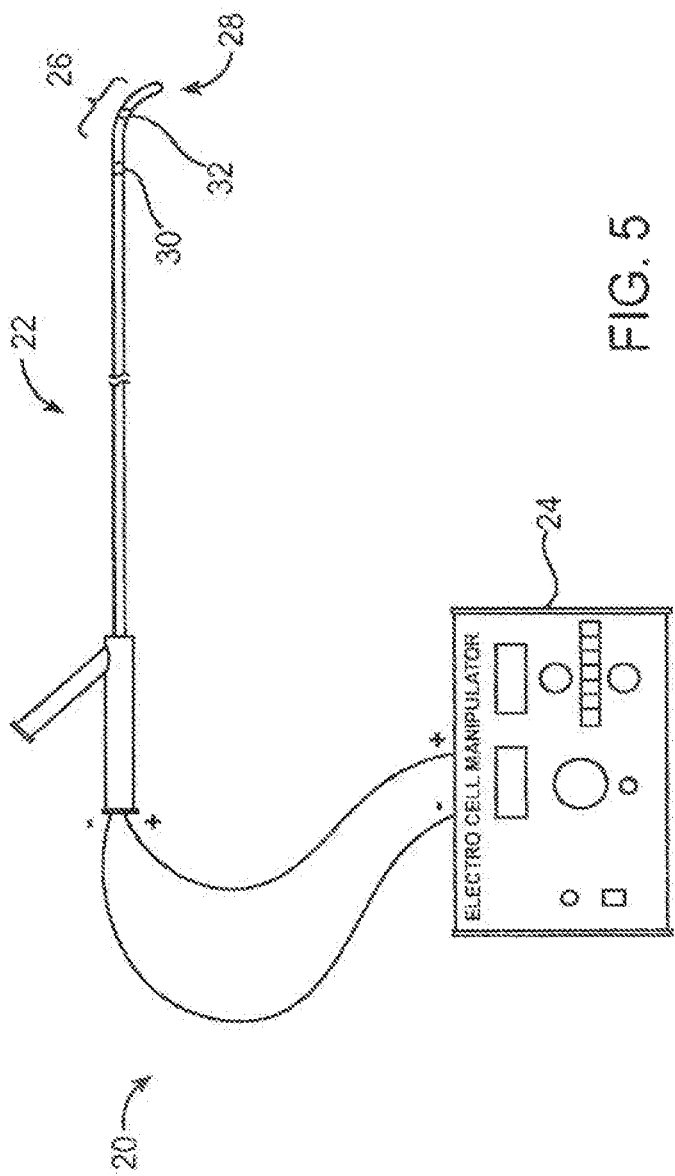
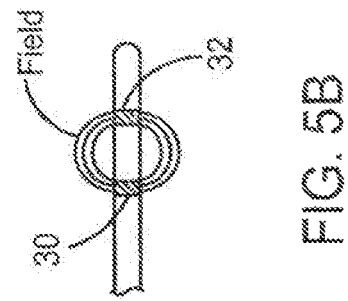
FIG. 5
FIG. 5A
FIG. 5B

SYSTEMS AND METHODS FOR DELIVERY OF A THERAPEUTIC AGENT

RELATED APPLICATIONS

This application is a continuation of application Ser. No. 16/036,381 filed Jul. 16, 2018, which in turn is a continuation of application Ser. No. 15/358,187 filed Nov. 22, 2016, now U.S. Pat. No. 10,022,529 issued Jul. 17, 2018, which in turn is a continuation of application Ser. No. 14/601,529 filed Jan. 21, 2015, now U.S. Pat. No. 9,498,283 issued Nov. 22, 2016, which in turn is a continuation of application Ser. No. 13/660,629 filed Oct. 25, 2012, now U.S. Pat. No. 8,961,391 issued Feb. 24, 2015, which in turn which is a continuation of application Ser. No. 13/253,595 filed Oct. 5, 2011, now U.S. Pat. No. 8,338,164 issued Dec. 25, 2012, which in turn is a continuation of application Ser. No. 12/559,278 filed Sep. 14, 2009, now U.S. Pat. No. 8,133,497 issued Mar. 13, 2012, which in turn is a divisional of application Ser. No. 11/459,090 filed Jul. 21, 2006, now U.S. Pat. No. 7,608,275 issued Oct. 27, 2009, which claims the benefit of U.S. Provisional Application No. 60/702,077 filed Jul. 22, 2005, each of which is hereby fully incorporated herein by reference. U.S. Pat. No. 7,608,275 also claims the benefit of, and incorporated by reference in its entirety U.S. Provisional Application No. and 60/747,771, filed on May 19, 2006, which is thereby also fully incorporated herein by reference.

BACKGROUND OF THE INVENTION

Field of the Invention

The present invention relates to methods and apparatus for the control of autonomic nerve function comprising delivery via permeabilization of targeted cell membranes a therapeutically effective amount of a portion or fragment of a neurotoxin such as botulinum toxin (BoNT), the active portion known as the light chain (LC), to cause a clinical benefit in various regions within the body.

First used for medical purposes over 20 years ago for treatment of blepharospasm and strabismus and other skeletal muscle abnormalities, certain neurotoxins have found widespread use in millions of patients worldwide for a variety of conditions.

Controlled injection of neurotoxins has become a common procedure to control skeletal muscle spasms. While the primary application of neurotoxins such as BOTOX®, commercially sold by Allergan, Inc. (Irvine, Calif.), has been focused on cosmetic applications, such as treatment of facial wrinkles, other uses for the compound are now common. Certain applications include treatment of cervical dystonia, tremor, headache (migraine), spasticity, torticollis, hemifacial spasm, blepharospasm, meige syndrome, spastic dysphonia, writers cramp, hyperhydrosis, hypersalivation, bladder dysfunction multiple sclerosis, spinal cord injury, cystic fibrosis, stroke paralysis, stuttering, and all types of pain.

*Clostridium botulinum* neurotoxins (BoNTs) block the release of acetylcholine from peripheral cholinergic nerve endings thereby disabling the release of neurotransmitters from the cells (Bigalke, H. and Shoer, L. F. (1999) Clostridial Neurotoxins in Handbook of Experimental Pharmacology 45, 407-443). This mechanism of action is well defined. Seven immunologically distinct serotypes of neurotoxin, designated types A through G, have been identified as discussed by Simpson, L. L., Schmidt, J. J. and Middlebrook, J. L. (1988) in Methods Enzymol. 165, 76-85. There are general structural and functional similarities among the various types of neurotoxins, but they all have preferred recipients, for example some favor use in humans and other in non-human species.

A frequently used neurotoxin for many applications in the human body is Botulinum Toxin Type A (BoNT\A), a protein produced by the bacterium *Clostridium botulinum* and sold commercially by Allergan, inc., as BOTOX®. Botulinum toxin blocks the release of neurotransmitter from the nerves that control the contraction of the target muscles. When used in medical settings, small doses of the toxin are injected into the affected muscles and block the release of a chemical acetylcholine that signals the muscle to contract. The toxin thus paralyzes or weakens the injected muscle.

In addition, use of neurotoxin for control of the following conditions has been proposed in U.S. Pat. No. 6,063,768 to First, and U.S. Pat. No. 5,766,605 to Sanders, including: rhinorrhea, asthma, COPD, excessive stomach acid secretion, spastic colitis, otitus media, arthritis, tensoynovitis, lupus, connective tissue disease, inflammatory bowel disease, gout, tumors, musculo-skeletal abnormalities, reflex sympathetic dystrophies, tendonitis, bursitis, and peripheral neuropathy. Various other patents contemplate the use of a neurotoxin for additional applications such as, neuromuscular disorders (U.S. Pat. No. 6,872,397), essential tremor (U.S. Pat. No. 6,861,058), pancreatitis (U.S. Pat. No. 6,843,998), muscle spasm (U.S. Pat. No. 6,841,156), sinus headache (U.S. Pat. No. 6,838,434), endocrine disorders (U.S. Pat. No. 6,827,931), priapism (U.S. Pat. No. 6,776,991), thyroiditis (U.S. Pat. No. 6,773,711), cardiovascular disease (U.S. Pat. No. 6,767,544), thyroid disorders (U.S. Pat. No. 6,740,321), hypocalcemia (U.S. Pat. No. 6,649,161), hypercalcemia (U.S. Pat. No. 6,447,785), tardive dyskenesia (U.S. Pat. No. 6,645,496), fibromyalgia (U.S. Pat. No. 6,623,742), Parkinson's Disease (U.S. Pat. No. 6,620,415) cerebral palsy (U.S. Pat. No. 6,448,231), inner ear disorders (U.S. Pat. No. 6,358,926), cancers (U.S. Pat. No. 6,139,845), otic disorders (U.S. Pat. No. 6,265,379), appetite reduction (US2004/0253274), compulsive disorders (US2004/0213814, US2004/0213813), uterine disorders (US2004/0175399), neuropsychiatric disorders (US2003/0211121), dermatological or transdermal applications (US2004/00091880), focal epilepsy (US2003/0202990) the contents of which are expressly incorporated herein by reference in their entirety.

The patent authors have further detailed devices and methods for treating asthma with local delivery of the intact botulinum toxin in U.S. patent application Ser. No. 10/437,882, filed on May 13, 2003, the contents of which are expressly incorporated by reference herein in its entirety.

Due to their extreme toxicity, neurotoxins are highly controlled and can have disastrous consequences if not used and controlled properly, especially when used in vivo. In addition, due to their toxicity, the body tends to build up a resistance to their use, resulting in lower efficacy, the need for increased treatments, or the need to discontinue their use all together in certain patients.

In light of the foregoing, it would be desirable to provide methods and apparatus for delivering neurotoxins such as botulinum toxins non-toxically.

It would also be desirable to provide methods and apparatus for treating various conditions with a neurotoxin such as botulinum toxin fragments via in vivo cell permeabilization.

In would also be desirable to provide a system of devices, including catheters, trocars, needles, endoscopes, inhalers, nebulizers and aerosolizers and other mechanisms to deliver fragmented neurotoxins non-toxically.

Further, it would be desirable to couple energy delivery devices with the delivery of fragmented neurotoxins to deliver active neurotoxins, non-toxically, including catheter based energy systems, and non-invasive energy systems.

All publications and patents or patent applications mentioned in this specification are herein incorporated by reference to the same extent as if each individual publication, patent or patent application was specifically and individually so incorporated by reference.

BRIEF SUMMARY OF THE INVENTION

According to the present invention, an active fragment (sometimes referred to as a catalytic portion) of a neurotoxin such as the botulinum neurotoxin (BoNT), preferably the light chain (LC) portion of BoNT, is delivered to target cells via cell membrane permeabilization. Such delivery provides a non-toxic delivery scheme for deriving a variety of clinical benefits. Although botulinum toxins are used broadly for a variety of clinical applications, the present invention provides enhanced methods of delivery and use of the isolated active fragments or portions of the toxin. Other neurotoxins which may be used in the methods and systems of the present invention include ricin and its active fragments, exotoxin A and its active fragments, diphtheria toxin and its active fragments, cholera toxin and its active fragments, tetanus toxin and its active fragments, and the like.

The present invention contemplates application to all of the conditions listed herein, collectively defined as "therapeutic target conditions", and any other conditions for which BoNT and other neurotoxins are known to or can be shown to provide a therapeutic benefit. Certain examples have been detailed below for specific applications, but it is within the scope of the present invention that the methods and devices detailed herein have specific applications to many or all of the conditions wherein the intact neurotoxins have shown or proposed to show a therapeutic benefit or effect.

In one aspect of the present invention, BoNT-LC or other active neurotoxin fragment is delivered with the application of energy to achieve cell membrane permeabilization.

In another aspect of the present invention methods and apparatus are provided for altering autonomic nerve function by utilizing an electric field or ultrasonic energy generated by a pulse or pulses of a designated duration and amplitude to alter tissue at the cellular level via permeabilization of the cell membrane to facilitate the translocation of the BoNT-LC or other active neurotoxin fragment to the cell cytosol.

A further aspect of the invention is to provide methods and apparatus for treating or inhibiting a variety of diseases or syndromes that have an underlying neurogenic component, by disrupting the neurogenic activities of the promoters or mediators of the disease or syndrome. Such disruption is facilitated by delivering an active fragment of botulinum toxin, such as the light chain portion of botulinum toxin serotype A (BoNT-LC/A), in the presence of an electric field or ultrasonic energy applied to permeabilize the wall of targeted cell under conditions which induce reversible poration of the cellular membrane and efficient passage of the BoNT-LC fragment to the cell cytosol, its catalytic environment.

In addition to the methods described thus far, the present invention further provides systems for delivering toxins to target cells in a mammalian host. The target cells may be in any of the target regions described above or in any other target region which may benefit from the specific and enhanced delivery of a neurotoxin to cells within the region. Systems comprise catheter or other structure adapted to introduce the toxin or toxin fragment to a region adjacent the target cells. The systems further comprise an energy applicator for applying energy to the target cells under condition which cause poration of the cell membranes to enhance delivery of the toxins and/or their active fragments. The systems still further comprise a source of the toxin or active fragments suitable for introduction from the catheter or other delivery structure.

The energy applicator will typically be adapted to selectively apply energy to target cells within the region where the toxin is to be introduced, e.g., by focusing energy distribution to the particular target cells or regions which are rich with the target cells. Alternatively, the energy applicator may be adapted to apply energy non-selectively within the target region where both target cells and other cell types may receive the energy.

In some instances, the toxin may comprise an intact toxin, but more usually will comprise an active toxin fragment as defined elsewhere in this application. In the exemplary embodiments, the active toxin fragment is the light chain fragment of the botulinum toxin (BoNT-LC). The light chain fragment may be derived from any one of at least botulinum toxins A, B, C, D, E, F, and G.

The energy applicators of the systems of the present invention may be adapted to apply electric energy, typically pulses between 1 V and 500 V to the targeted region. The electric energy may be radiofrequency (RF) energy, where the energy may be pulsed for durations between 5 microseconds to 100 milliseconds. Alternatively, the electrical energy can be direct current (DC), alternating current (AC), or combinations thereof.

'In addition to electrical energy, the energy applicator may be adapted to deliver ultrasonic energy, X-ray beam energy, microwave energy, or any other energy type which can achieve a reversible poration of the target cell walls.

There are at least two general power categories of medical ultrasound waves which may be utilized in the present invention. One category of medical ultrasound wave is high acoustic pressure ultrasound. Another category of medical ultrasound wave is low acoustic pressure ultrasound. Acoustic power is expressed in a variety of ways by those skilled in the art. One method of estimating the acoustic power of an acoustic wave on tissue is the Mechanical Index. The Mechanical Index (MI) is a standard measure of the acoustic output in an ultrasound system. High acoustic pressure ultrasound systems generally have a M1 greater than 10. Low acoustic pressure systems generally have a MI lower than 5. For example, diagnostic ultrasound systems are limited by law to a Mechanical Index not to exceed 1.9. Another measurement used by those skilled in the art is the spatial peak, peak average intensity (Isppa). The intensity of an ultrasound beam is greater at the center of its cross section than at the periphery. Similarly, the intensity varies over a given pulse of ultrasound energy. Isppa is measured at the location where intensity is maximum averaged over the pulse duration. Isppa for high acoustic pressure or high intensity focused ultrasound (HIFU) applications ranges from approximately 1500 W/cm$^2$ to 9000 W/cm$^2$. Diagnostic ultrasound equipment, for instance, will generally have, and an Isppa less than 700 W/cm$^2$. Yet another way in which ultrasound waves can be characterized is by the amplitude of their peak negative pressure. High acoustic pressure or HIFU applications employ waves with peak amplitudes in excess of 10 MPa. Low acoustic pressure ultrasound will generally have peak negative pressures in the range of 0.01 to 5.0 MPa. Diagnostic ultrasound equipment, for example, will generally have a peak amplitude less than 3.0 MPa.

Both high and low acoustic pressure ultrasound systems generally operate within the frequency range of 20 KHz-10.0 MHz Interventional applications (such as in blood vessels) operate clinically up to about 50 MHz. Also opthalmologic applications up to about 15 MHz. Diagnostic imaging typically uses frequencies of about 3 to about 10 MHz. Physical therapy ultrasound systems generally operate at frequencies of either 1.0 MHz or 3.3 MHz. High acoustic pressure ultrasound or high intensity focused ultrasound has been used for tissue disruption, for example for direct tumor destruction. High intensity focused ultrasound using high acoustic pressure ultrasound is most commonly focused at a point in order to concentrate the energy from the generated acoustic waves in a relatively small focus of tissue.

Systems and methods for permeabilization of target tissue cell membranes according to the present invention may employ either high acoustic pressure or low acoustic pressure ultrasound. Some embodiments may preferably employ relatively low acoustic pressure, for example the systems described herein where the transducers are mounted on the delivery devices and operate inside the body. Other systems may operate at interim acoustic pressure ranges. For example, systems described herein which employ an external ultrasound generator and transducer and which conduct the ultrasound to the target tissues through the use of a wave guide. In these systems, losses due to transduction through the wave guide can be compensated for by increasing the input power to the wave guide until adequate power is delivered to the target tissue. Finally, some systems described herein may employ focused or partially focused higher pressure ultrasound, for example the systems which employ an external mask to conduct the ultrasonic power through the tissues to the target tissues. It should be appreciated that combinations of high and low acoustic pressure systems may also be employed.

The catheter or other structure may be adapted to introduce the toxin to the target cells in a variety of ways. For example, catheters may comprise a needle for injecting the toxin, optionally a needle which is deployable axially or radially from the catheter body. Alternatively or additionally, catheters may be provided with nozzles or other ports for aerosolizing the toxin, particularly within regions of the lung as described herein. Still further alternatively or additionally, the catheters may comprise balloons or other expandable elements for deflecting an end of the catheter to engage one or more ports on the catheter against the tissue where the toxin fragments are released through the port(s). In a specific embodiment, the ports may be in the balloon itself where the toxin fragments are released through the ports in the balloon as the balloon is inflated with the medium containing the fragments. With such balloon embodiments, the electrodes or other energy transducers will typically be located within the balloon for applying the poration energy to the target tissue. Further optionally, the energy applicators may be mounted directly on the catheters, for example in the form of acoustic transducers, RF or other electrical electrodes, or the like. Alternatively, the energy applicator may be provided separately from the toxin delivery catheter or other source, typically being an external source, such as an external high intensity focused ultrasound (HIFU) source or an external electrode array for delivering radiofrequency or other electroporation energy.

In a further aspect of the invention, it may be desirable to provide methods and devices that utilize a non-toxic delivery mechanism to target cells to reduce the potential for an immunogenic response to the delivered toxin over time.

In a further aspect of the invention, it may be desirable to deliver the therapeutic neurotoxin fragment and energy via a catheter.

In a further aspect of the invention, it may be desirable to deliver the therapeutic neurotoxin fragment via an aerosolizer or nebulizer.

In a further aspect of the invention, it may be desirable to deliver the therapeutic neurotoxin fragment via an inhaler.

In a further aspect of the invention, it may be desirable to deliver the therapeutic neurotoxin fragment and membrane transport energy transdermally.

In a further aspect of the invention, it may be desirable to deliver the therapeutic neurotoxin fragment via a catheter, or aerosolizer or inhaler, and the energy via a catheter placed in the vicinity of the targeted cell.

In a further aspect of the invention, it may be desirable to deliver the therapeutic neurotoxin fragment and the membrane transport energy via an implantable generator and drug delivery pump.

In a further aspect of the invention, it may be desirable to deliver the therapeutic neurotoxin fragment via a catheter, or aerosolizer (nebulizer) or inhaler, and the energy via an external energy source adapted to target the applied energy in the vicinity of the targeted cell.

BRIEF DESCRIPTION OF THE DRAWINGS

Further features of the invention, its nature and various advantages will be more apparent from the accompanying drawings and the following detailed description, in which:

FIG. 1—depicts a schematic of the creation of neurotoxin Botulinum Toxin Type A (BoNT/A), including the light chain (LC) fragment or portion.

FIGS. 5, 5A-5B—depicts various embodiments of a delivery device of the present invention utilizing multiple energy transmission elements and an energy transmission system.

DETAILED DESCRIPTION OF THE INVENTION

Figure 2A:
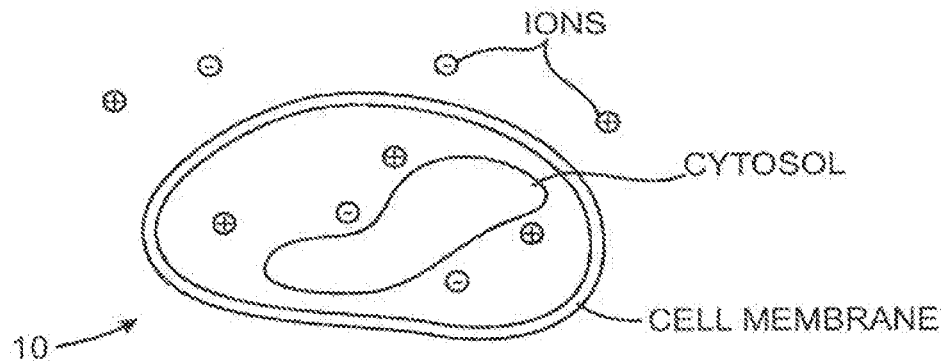
FIG. 2A—depicts a schematic of a target cell, including the cell membrane, and inner cellular matrices.

The present invention is directed to methods and apparatus for targeting the non toxic delivery of a fragment of a neurotoxin, while still maintaining the catalytic or toxic effect of the neurotoxin fragment once it is non-toxically delivered to its targeted cell. For purposes of this specification, the term "non-toxic", "non-toxically" and the like refer to the state of the fragment molecule prior to delivery to a target location. In this description, the fragment neurotoxin is intended to retain its toxic effect once delivered to its catalytic environment; the intracellular matrix or cytosol of the targeted cell.

Devices and methods of the present invention may be directed to suitable "targeted regions" such as muscle cells in various regions of the body related to the various "therapeutic target conditions" or syndromes to be treated, as detailed in this specification above. Some particular examples include targeting mucosal and muscular lining of the lung, cholinergic cells in the region of tumors, myofacial regions, vascular smooth muscle cells, musculoskeletal regions and the like.

According to the present invention, energy fields (EF) may be applied to target regions in conjunction with the delivery of a fragmented neurotoxin such as BoNT-LC to facilitate the transfer of the neurotoxin fragment into the targeted cell, non-toxically via in vivo target cell permeabilization.

Use of Isolated Light Chain of Botulinum Neurotoxins

Figure 1:
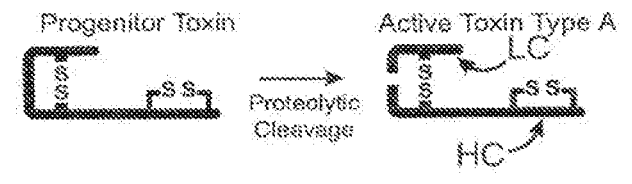

Generally, the BoNT molecule is synthesized as a single polypeptide chain of 150 kD molecular weight. The neurotoxin is then exposed to enzymes, either during cultivation of the *Clostridium botulinum* organism or subsequent to purification of the toxin, wherein specific peptide bonds are cleaved or "nicked" resulting in the formation of a dichain molecule referred to as BoNT. As shown in FIG. 1, dichain neurotoxin is composed of a light chain (LC) region 50 kD molecular weight linked by disulfide bonds to a heavy chain (HC) 100 kD molecular weight (Kistner, A., Habermann, E. (1992) *Naunyn Schmiedebergs Arch. Pharmacol.* 345, 227-334). When the light chain is separated from the heavy chains of botulinum toxin, neither chain is capable of blocking neurotransmitter release, however, the light chain alone is capable of blocking acetylcholine release if transported directly into the cell cytosol. (Ahnert-Hilger, G., Bader, M. F., Bhakdi, S., Gratzl, M. (1989) *J. Neurochem.* 52, 1751-1758 and Simpson, L. L. (1981) *Pharmacol. Rev.* 33, 155-188.) Focusing on the light chain, the isolation or separation process essentially renders the light chain "non-toxic" in a general environment, while still maintaining its effect or toxicity, once it is transported through the target cell membrane.

Over the past several years, the separation and purification of the light chain and heavy chain of BoNT has seen significant development activity. In the case of the heavy chain (HC), researchers are interested in its ability to bond with a target cell and deliver certain molecules into that cell. For example, various drug delivery applications have been suggested, for example, using the HC to bind to tPA so that a patient could inhale the HC bound tPA allowing it to cross the membrane of the lungs and be transported into the bloodstream for anticoagulation. Of particular interest to the present invention are the efforts to isolate and purify the light chain (LC) of the botulinum molecule. In its isolated and purified form, all HC elements are removed, rendering the LC incapable of crossing the cell membrane without assistance. Thus, the LC is non-toxic until delivered to the target cell cytosol by the delivery protocols of the present invention.

Various groups have been active in the area of isolation and purification. For example, companies such as Metabiologics, a group affiliated with the University of Wisconsin, the Center for Applied Microbiology and Research (CAMR), a division of the UK Health Protection Agency, List Biological Laboratories, Inc. of California, and other research groups throughout the world. Many of these companies provide purified preparations of botulinum neurotoxins from *Clostridium botulinum* types A and B. List Laboratories in particular provides recombinantly produced light chains from both types A, B, C, D and E.

According to the present invention, the therapeutic use and delivery of the light chain only may significantly improve the safety profile of certain applications of therapies utilizing BoNT. BoNT are some of the most lethal toxins known to man. All concerns about migration of the neurotoxin into unintended regions, and harm or toxicity to the patient or physician are eliminated by storing, handling, injecting and metabolizing the light chain only. In the absence of a specific membrane binding technology, the LC is completely non-toxic. In certain applications, such as the treatment of asthma, this is of critical import. In using BoNT to treat asthma, a large quantity of the purified LC substance may be introduced directly into the lung, and then specifically transported to target cells in the exact location and only during the period of use of application of the membrane transport technology, such as cell membrane permeabilization by energy. Once the membrane transport technology has been removed, turned off or otherwise inactivated, the remaining LC which has not been transported into target cells can simply be removed from the body by standard biologic processes for expelling foreign materials, e.g. coughing, immune system or lymphatic system transport and the like.

In addition, therapeutic use of only the LC of the neurotoxin BoNT may reduce the likelihood of the body developing an immunogenic response to the therapy that is seen with delivery of the intact toxin. This could be a major advantage in light of the repetitive application or injection of the toxin that is required to maintain a therapeutic effect.

Non-Toxic Membrane Transport Mechanisms

To date, the main application of purified or isolated light chain has been the study of its mechanism of action. To further this research, literature has reported the use of certain detergent based permeabilization techniques to deliver fragment BoNT (Bittner M A, DasGupta B R, Holz R W. Isolated light chains of botulinum neurotoxins inhibit exocytosis. Studies in digitonin-permeabilized chromaffin cells. J Biol Chem 1989 Jun. 25; 264 (18):10354-10360.) Further reference to the mechanism of permeability of cell membranes to deliver botulinum toxin are mentioned in U.S. Pat. No. 6,063,768 to First, and U.S. Pat. No. 6,632,440 to Quinn, Chaddock, et al "Expression and Purification of Catalytically Active Non-Toxic Endopeptidase Derivatives of *Clostridium botulinum* toxin type A", *Protein Expression and Purification*, 25 (2002) 219-228, contemplating the insertion of the light chain of BoNT into a target cell without the heavy chain for purposes of deriving vaccines or in bench top studies of cell mechanisms of action. The contents of these references are expressly incorporated by reference in their entirety. None of the teachings contemplate a delivery of a fragment of neurotoxin using a clinically acceptable permeabilization technique in vivo for therapeutic uses as is contemplated by the present invention.

For purposes of this specification, the term "poration" includes various forms of electroporation, such as the use of pulsed electric fields (PEFs), nanosecond pulsed electric fields (nsPEFs), ionophoreseis, electrophoresis, electropermeabilization, as well as other energy mediated permeabilization, including sonoporation (mediated by ultrasonic or other acoustic energy), and/or combinations thereof, to create temporary pores in a targeted cell membrane. Similarly, the term "electrode" or "energy source" used herein, encompasses the use of various types of energy producing devices, including x-ray, radiofrequency (RF), DC current, AC current, microwave, ultrasound, adapted and applied in ranges to produce membrane permeabilization in the targeted cell.

Reversible electroporation, first observed in the early 1970's, has been used extensively in medicine and biology to transfer chemicals, drugs, genes and other molecules into targeted cells for a variety of purposes such as electrochemotherapy, gene transfer, transdermal drug delivery, vaccines, and the like.

In general, electroporation may be achieved utilizing a device adapted to activate an electrode set or series of electrodes to produce an electric field. Such a field can be generated in a bipolar or monopolar electrode configuration. When applied to cells, depending on the duration and strength of the applied pulses, this field operates to increase the permeabilization of the cell membrane and reversibly open the cell membrane for a short period of time by causing pores to form in the cell lipid bilayer allowing entry of various therapeutic elements or molecules, after which, when energy application ceases, the pores spontaneously close without killing the cell after a certain time delay. As characterized by Weaver, *Electroporation: A General Phenomenon for Manipulating Cells and Tissues* Journal of Cellular Biochemistry, 51:426-435 (1993), short (1-100 .mu.s) and longer (1-10 ms) pulses have induced electroporation in a variety of cell types. In a single cell model, most cells will exhibit electroporation in the range of 1-1.5V applied across the cell (membrane potential).

In addition, it is known in the art that macromolecules can be made to cross reversibly created pores at voltages of 120V or less applied to cells for durations of 20 microseconds to many milliseconds. For applications of electroporation to cell volumes, ranges of 10 V/cm to 10,000 V/cm and pulse durations ranging from 1 nanosecond to 0.1 seconds can be applied. In one example, a relatively narrow (pee) high voltage (200V) pulse can be followed by a longer (>msec) lower voltage pulse (<100V). The first pulse or series of pulses open the pores and the second pulse or series of pulses assist in the movement of the BoNT-LC across the cell membrane and into the cell.

Certain factors affect how a delivered electric field will affect a targeted cell, including cell size, cell shape, cell orientation with respect to the applied electric field, cell temperature, distance between cells (cell-cell separation), cell type, tissue heterogeneity, properties of the cellular membrane and the like.

Various waveforms or shapes of pulses may be applied to achieve electroporation, including sinusoidal AC pulses, DC pulses, square wave pulses, exponentially decaying waveforms or other pulse shapes such as combined AC/DC pulses, or DC shifted RF signals such as those described by Chang in *Cell Potation and Cell Fusion using and Oscillating Electric Field*, Biophysical Journal October 1989, Volume 56 pgs 641-652, depending on the pulse generator used or the effect desired. The parameters of applied energy may be varied, including all or some of the following: waveform shape, amplitude, pulse duration, interval between pulses, number of pulses, combination of waveforms and the like.

Figure 2B:
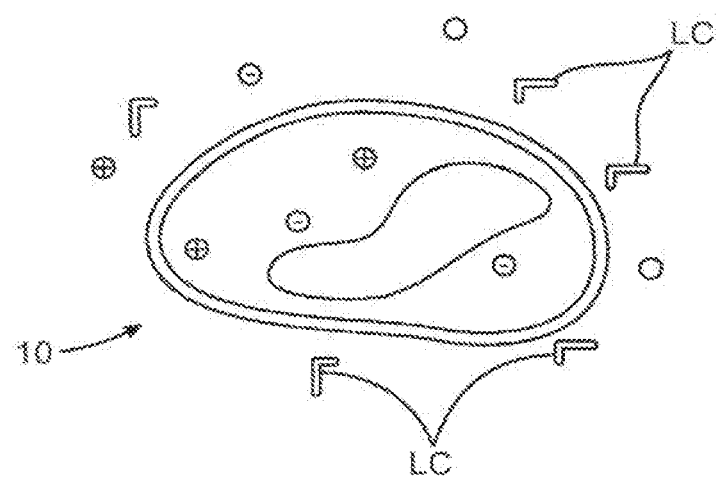
FIG. 2B—depicts a schematic of the target cell wherein LC molecule has been introduced.
Figure 3A:
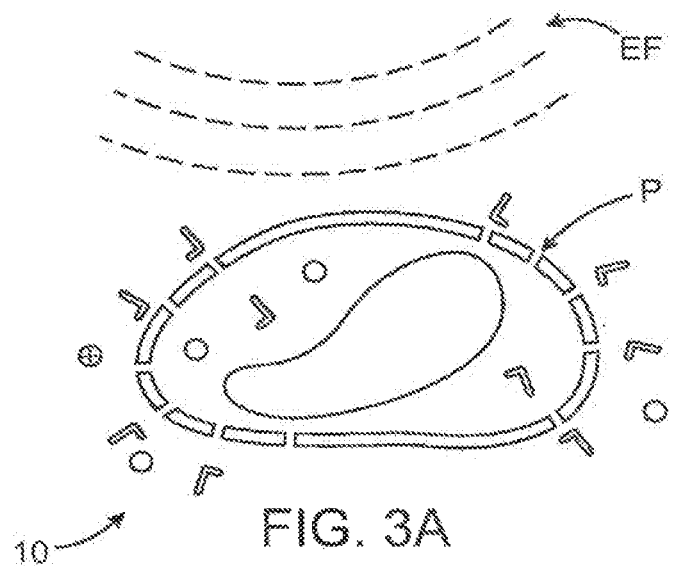
FIG. 3A-3B—depicts a the target cell of FIG. 2 showing application of an energy field (EF) to produce permeabilization or pores (P) in the cell membrane, and introduction of the LC fragment therethrough.
Figure 3B:
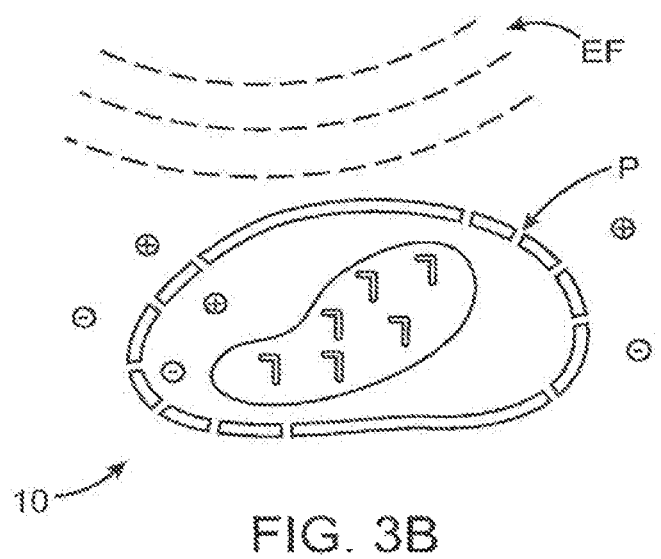
Figure 4:
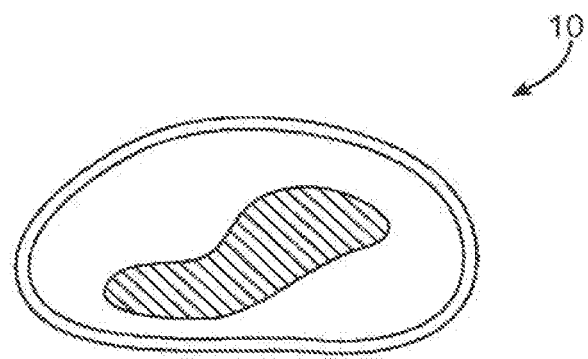
FIG. 4—depicts a schematic of a cell wherein the energy field has been discontinued, and neurotransmission of the cell has been effectively blocked.

A schematic example of the methods of the present invention are shown in FIGS. 2-4 in a simplified single cell model. A targeted cell 10 is shown in FIG. 2A. Fragmented neurotoxin such as BoNT-LC (LC) is introduced into the vicinity of the targeted cell as depicted in FIG. 2B. An energy field (EF) is applied in accordance with the present invention resulting in the transfer of the BoNT-LC through pores P to the intracellular matrix (cytosol) as shown in FIGS. 3A and 3B. Once this transfer has occurred, the release of neurotransmitters of the target cell are then blocked or disrupted, and once energy application is discontinued, the pores P in the cell membrane recover or close as depicted in FIG. 4.

Of particular interest for application in certain therapeutic target conditions is the developing field of sonoporation. Just as pulses of high voltage electricity can open transient pores in the cell membrane, ultrasonic energy can do the same. See for example Guzman et al. "Equilibrium Loading of Cells with Macromolecules by Ultrasound: Effects of Molecular Sizing and Acoustic Energy," Journal of Pharmaceutical Sciences, 91:7, 1693-1701, which examines the viability of ultrasound to deliver molecules of a variety of sizes into target cells. In addition, techniques for nebulizing fluids and aqueous drugs are well known in the art, and as such, devices of the present invention may be adapted to introduce a BoNT-LC solution to a target region, such as the lung and then effect selective membrane transport of the BoNT-LC into the cell using sonoporation.

For example, U.S. Pat. No. 6,601,581 to Babaev, hereby incorporated by reference in its entirety, describes certain techniques for delivering therapeutic agents using ultrasound for pulmonary delivery via an aerosolizing technique. Further, Guzman, et al, depicts delivery of molecules from a low of 62 Da up to 464 kDa (a range of 0.6-18.5 nm radius). Since the LC of the botulinum toxin is in the 50 kDa range, the LC would be very susceptible to sonoporetic delivery. Furthermore, Guzman, et al also showed that for all size ranges tested, levels of macromolecule within the cell reached thermodynamic equilibrium with the extracellular environment, and the cell uptake also depended on the energy delivered, as expressed in J/cm2. As such, the sonoporetic delivery of LC to the targeted regions may be controlled by adjusting the concentration of the LC exposed to the target region (e.g. wall or membrane of the lung), the energy delivered to the target region, or both.

Catheter Devices

To achieve the goals of the present invention, it may be desirable to employ methods and apparatus for achieving cell membrane permeabilization via the application of an energy source, either from a catheter located directly in the vicinity of the targeted cells, or an externally focused energy system. For purposes of this specification, the term "catheter" may be used to refer to an elongate element, hollow or solid, flexible or rigid and capable of percutaneous introduction to a body (either by itself, or through a separately created incision or puncture), such as a sheath, a trocar, a needle, a lead. Further descriptions of certain electroporation catheters are described in U.S. Patent Application 60/701, 747, filed on Jul. 22, 2005, the full disclosure of which is expressly incorporated herein by reference.

FIGS. 5 and 5A-5B depict a system 20 utilizing an electroporation catheter 22 for selective electroporation of targeted cells. In certain configurations of the present invention, voltages may be applied via the electroporation catheter 22 to induce reversible electroporation at the same time as the catheter delivers the fragmented neurotoxin to the targeted region.

Referring to FIG. 5, electroporation catheter system 20 further comprises a pulse generator 24 such as those generators available from Cytopulse Sciences, Inc. (Columbia, Md.) or the Gene Pulser Xcell (Bio-Rad, Inc.), or IGEA (Carpi, Italy), electrically connected to a catheter having a proximal end and a distal end and adapted for minimally invasive insertion into the desired region of the body as described herein. The catheter further comprises an electroporation element 26 at a distal 28 end thereof. The electroporation element may include for example a first and second electrode 30 and 32 operatively connected to the pulse generator for delivering the desired number, duration, amplitude and frequency of pulses to affect the targeted cells. These parameters can be modified either by the system or the user, depending on the location of the catheter within the body (intervening tissues or structures), and the timing and duration of reversible cell poration desired. FIG. 5A depicts an arrangement of electrodes 30 and 32 that produces an electric field concentrated in a lateral direction from the catheter body whereas, FIG. 5B shows a device constructed to create a more uniform electric field about the shaft of the catheter body.

Figure 6A:
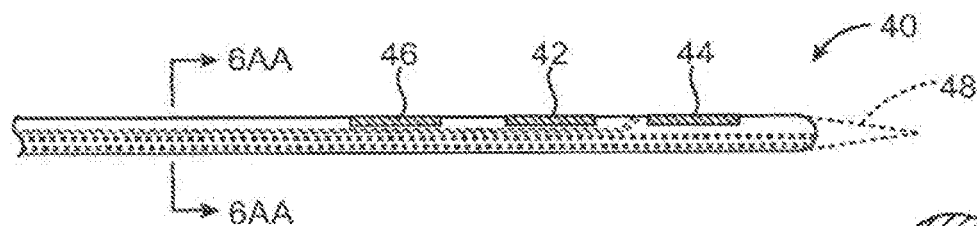
FIGS. 6A-D, 6AA, and 6CC—depict various electrode catheter configurations adapted to deliver energy or energy and therapeutic agents to target tissue.
Figure 6A:
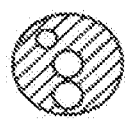

Further catheter device and electrode configurations are shown in FIGS. 6A-6D. FIG. 6A depicts an elongate catheter 40 having first and second electrodes 42 and 44 near the distal tip thereof, and including a monitoring or stimulation electrode 46 in the vicinity of the active porating electrodes for localizing the treatment area. In some embodiments, the monitoring or stimulating function may be performed by one or more of the treatment electrodes. The catheter device may have an optional sharp tip 48 to facilitate percutaneous introduction. Cross-sectional view FIG. 6AA shows various lumens provided for neurotoxin fragment delivery and other purposes.

Figure 6B:
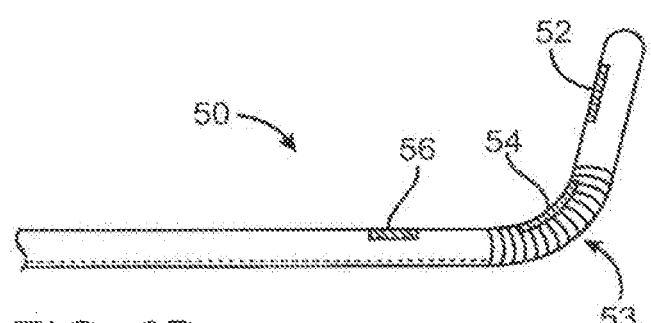

FIG. 6B is a similar catheter device 50 having electrodes 52, 54, and 56, but is further adapted to be steerable, or articulate at a region 53 near the distal end of the device, e.g., including a pull wire for deflecting the tip. Such steering ability enables the operator to introduce the device into tight or tortuous spaces (such as the bronchial passages or cardiovascular vessels) so that optimal placement of the device at the target location may be achieved.

Figure 6C:
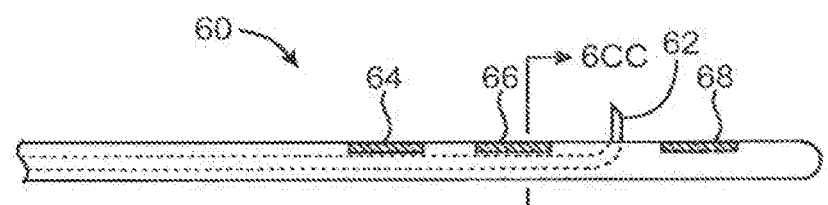
Figure 6C:
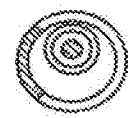

FIG. 6C depicts a catheter device 60 having a needle 62 or other injection element to allow for the injection of a therapeutic agent such as a fragmented neurotoxin before, during or after the application of the pulsed energy or electroporation. The catheter 60 further includes electrodes 64 and 66 or other poration components as discussed herein.

Figure 10:
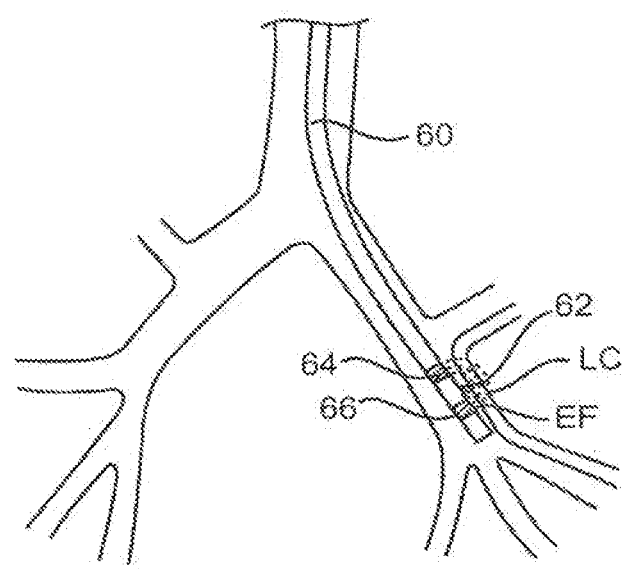
FIG. 10—depicts an interstitial method of use of the present invention.

The injection element may be a needle 62 as shown in FIG. 6C, an infusion port, or other infusion means. Needle 62 may also be used as an electrode in addition to an injection port. Electrode 68 comprises a monitoring or stimulating electrode. FIG. 10 depicts the use of a catheter of FIG. 6C to treat bronchial tissue in the lung for a variety of respiratory ailments such as asthma. FIG. 6CC is a cross-sectional view taken along line 6CC-6CC in FIG. 6, showing a co-axial sleeve design.

Figure 6D:
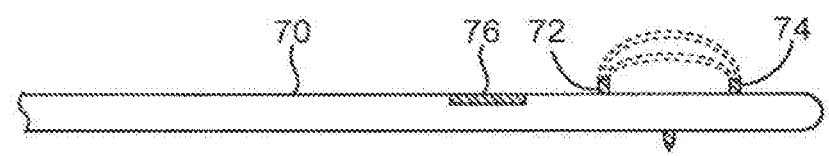

FIG. 6D depicts a catheter device 70 having electrode elements 72 and 74 that are adapted to extend laterally from the main catheter body, and in some cases, penetrate the surrounding tissue prior to application of energy. In doing so the depth and direction of the energy field created by the electroporative process, may be further controlled. A monitoring/stimulating electrode 76 will usually also be provided. Elements 72 and 74 may also be used as injection ports for introduction of toxin or toxin fragments.

Figure 7:
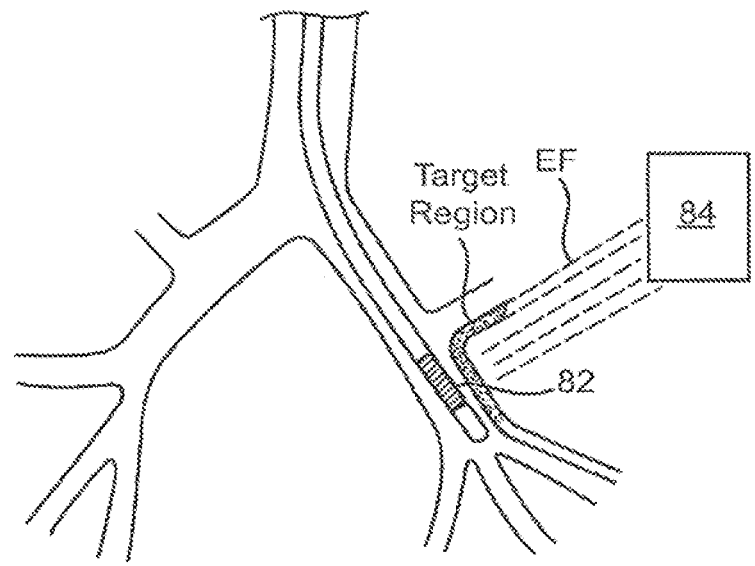
FIG. 7—depicts an alternative embodiment of the present invention wherein one of the multiple energy transmission elements is placed at the targeted cell site, and the other in a location remote therefrom.

FIG. 7 depicts the use of a catheter device 80 of the present invention for treatment of a respiratory tract, by positioning at least one electrode (82) at the target region, and a second electrode (84) remote from the target region, the target region being positioned between 82 and 84, such that activation of the electrodes produces an energy field (EF) therebetween, the size and intensity of which can be controlled by the placement of the electrodes relative to each other and the targeted region.

Figure 8:
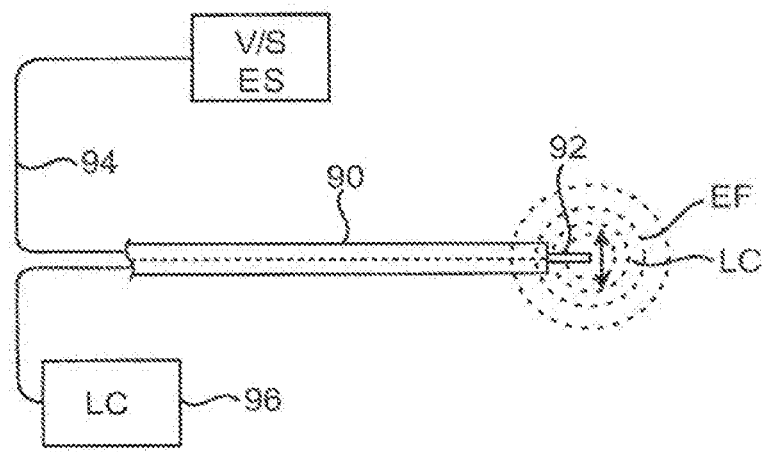
FIG. 8—depicts an embodiment of the present invention utilizing an ultrasound element on a catheter device.
Figure 11:
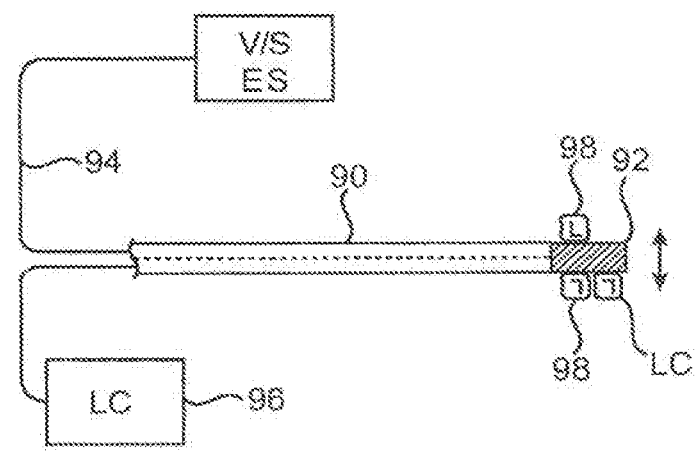
FIG. 11—depicts an embodiment of the present invention utilizing an aerosolizing element.

FIG. 8 depicts catheter 90 constructed in accordance with the principles of the present invention utilizing an ultrasonic element 92 that may be particularly useful in delivery of the BoNT-LC to bronchial tissue (lung) that provides a broad but targeted transport of the LC across the target cell walls, for example, epithelial and goblet cell walls. In this device, ultrasound energy is delivered to the distal end of the catheter device via an ultrasonic waveguide 94 that is operatively connected to an ultrasound energy source (U/SES). The LC fragment would be delivered from a receptacle 96 via the same lumen as the waveguide via a lumen provided the distal tip of the device. In operation, the ultrasonic energy would cause the LC solution to be nebulized, forming a mist or aerosol 98 within the lung, as shown in FIG. 11. The aerosol 98 itself, in the appropriate concentrations, may act as an ultrasound coupler, conveying the ultrasonic energy to the wall of the lung or other targeted cellular structures, causing sonoporation of the targeted cells whereby the LC fragment is transmitted across the cell membranes to become an effective neurotransmitter blocker. In an alternative embodiment, an ultrasonic transducer may be located directly at the tip of the delivery device, eliminating the need for a wave guide. Various catheters useful for delivering vibrational energy to tissue are described in U.S. Pat. Nos. 6,361,554 and 6,464,680 to Brisken, the contents of which are expressly incorporated herein by reference in their entirety, for various therapeutic effects, such as enhancing cellular absorption of a substance.

Since air is a very effective insulator against transmission of ultrasonic energy, the treatment area in the lung may be more precisely controlled by the concentration of the LC mist and the intensity of the ultrasonic energy. A fairly steep drop off in energy delivery would occur as mist concentration diffused, effectively protecting areas outside the predetermined radius surrounding the distal end of the delivery device. According to the present invention, since no functional neurotoxin exists without an effective membrane transport technology, terminating the energy application leaves a harmless mist that is then coughed up (if resident in the lungs) or otherwise metabolized and excreted by the body.

Any of the catheter devices described herein, or described in the contemporaneously filed U.S. Patent Application 60/701,747, previously incorporated by reference in its entirety, may be adapted to include an energy delivery element such as those described herein for purposes of providing a membrane transport system for delivery of a fragment of neurotoxin. In addition, certain catheter devices and methods such as those set forth in U.S. Pat. Nos. 5,964,223 and 6,526,976 to Baran may be adapted to include energy transmission elements capable of producing a porative effect at the cellular level, including electrodes, ultrasonic elements and the like, for treatment in the respiratory tract.

Furthermore, any of the foregoing systems may include electrodes or other monitoring systems either located on the treatment catheter, or external to the patient, to determine the degree of treatment to the region, including, thermocouple, ultrasound transducers, fiberoptics, sensing or stimulating electrodes. Further, it may be desirable to incorporate multiple pairs of electrodes that may be activated in pairs, in groups, or in a sequential manner in order to maximize the desired shape of the energy field (EF) while minimizing the field strength requirements.

Implantable Devices

Figure 12:
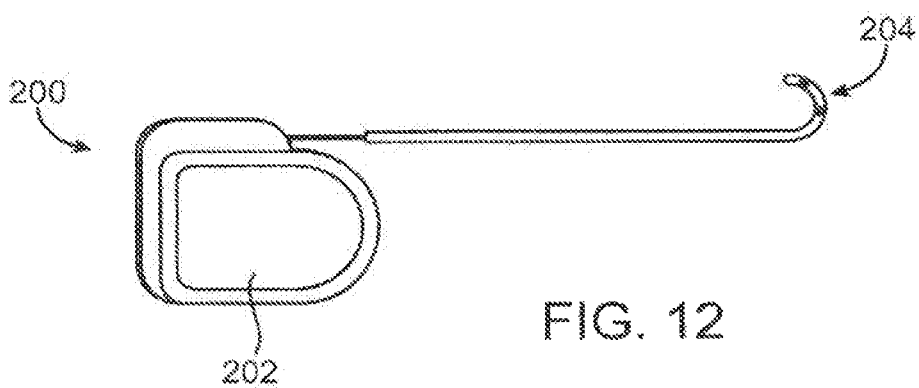
FIG. 12—depicts a fully implantable pulse generator, lead and agent delivery pump of the present invention.

Just as energy may be delivered to a targeted region to facilitate the delivery of fragmented neurotoxin via a catheter system, it is also within the scope of the present invention to deliver neurotoxins via an implantable system, including a pulse generator, lead and drug pump as depicted in FIG. 12. A neuromodulation system 200 may be fully implantable, having a pulse generator and a power supply or battery and be operatively connected to a programmable drug delivery pump all housed within a module 202, including a reservoir in which the BoNT-LC is stored for delivery over time using the principles of the present invention and technology of the programmable drug pump. A catheter 204 can be adapted to deliver the drug and poration energy to a desired target location in the patient's body.

Examples of useful implantable devices of the present invention are, devices such as those set forth in U.S. Pat. No. 5,820,589 to Torgerson et al, the entire contents of which are hereby incorporated by reference, the SynchroMed® programmable pump available from Medtronic, Inc. (Minneapolis, Minn.), and the neurostimulation units such as the RESTORE* or SynergyPlus® available from Medtronic, Inc., modified if necessary to deliver the desired voltage range for cell membrane permeabilization. Implantation of the neurostimulation device is further described in U.S. Pat. No. 6,847,849, incorporated herein by reference in its entirety.

The non-toxic nature of the BoNT in the absence of applied energy makes it possible to contemplate placing a bolus of neurotoxin in the body of a patient in what might otherwise be a toxic amount. This is particularly advantageous, since the traditional treatment regime using neurotoxins, is typically repeat injections of the toxins every 3 to 6 months and sometimes more frequently depending on the application. Certainly in more chronic conditions such as chronic pain, tremor, spasm, palsy and the like, such a fully implantable system may be highly desirable.

Non-Invasive Devices

It is within the scope of the invention to deliver either the energy or the therapeutic BoNT-LC non-invasively, or both.

Figure 13:
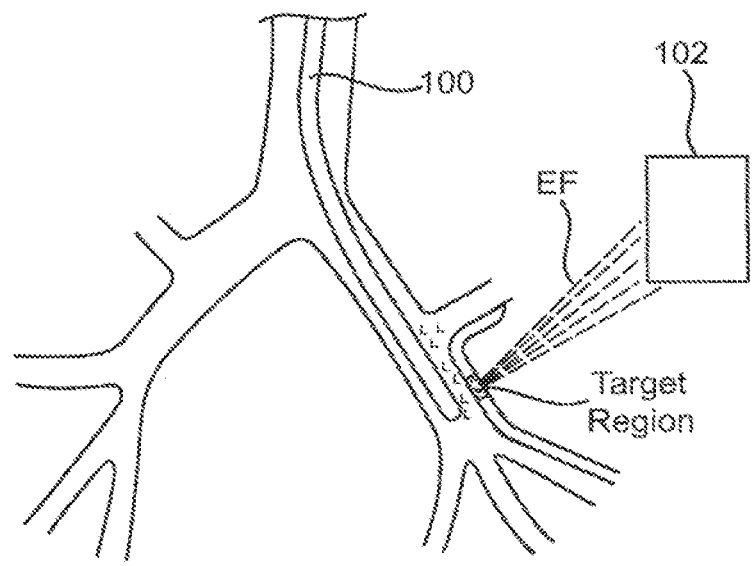
FIG. 13—depicts an embodiment of the present invention utilizing an external energy delivery source applied to the therapeutic agent applied in the vicinity of a targeted cell.
Figure 9:
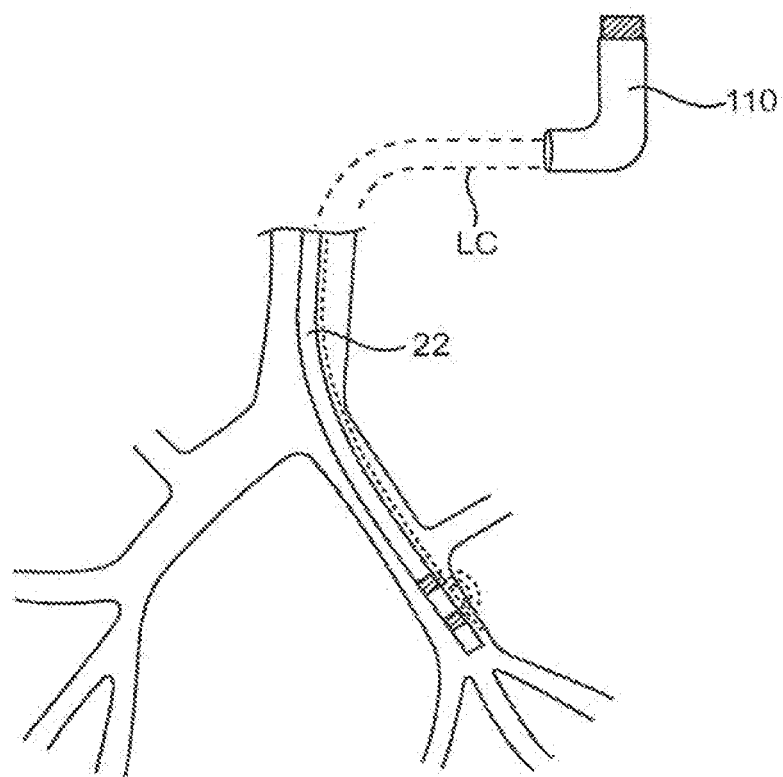
FIG. 9—depicts an embodiment of the present invention utilizing an inhaler with an in vivo energy delivery source.

For example, FIG. 13 depicts delivery of the BoNT-LC via a catheter 100 placed in the bronchial passageway with the energy field (EF) delivered from outside the patient in the form of an energy system 102 such as focused ultrasound (HIFU), stereotactic x-ray beams, magnetic resonance transmission, and the like. As detailed in U.S. Pat. Nos. 6,626,855 and 6,719,694 to Weng, the contents of which are expressly incorporated herein by reference in their entirety, an ultrasound beam can be controlled from outside the patient to focus the ultrasound beam in the desired location and intensity. For use in the present invention, it may be desirable to pulse or otherwise attenuate the ultrasound beam to achieve reversible cellular poration at the targeted site. Further, due to its non-toxic state, the BoNT-LC may be inhaled by the patient using a standard inhaler device such as those using pressurized aerosols known as metered dose inhalers (MDI) available from Cardinal Health (Somerset, N.J.), the OPTIHALER® available from National Allergy Supply Incorporated (Georgia, USA), or a nebulizer breathing machine such as a Pari DURANEB 3000 portable nebulizer available from Medinfinity, Co. (Fountain Valley, Calif.). In addition, certain technology currently under development employing thermal aerosols, such as a the STACCATO™ vaporization technology from Alexza Molecular Delivery (Palo Alto, Calif.) may also be useful within the scope of the present invention. Such devices 110 may be used as depicted in FIG. 9 for treating a respiratory ailment such as asthma. Optionally, the drug can be delivered with the catheter 22 (as shown) or with the external sources of FIG. 13.

Figure 15:
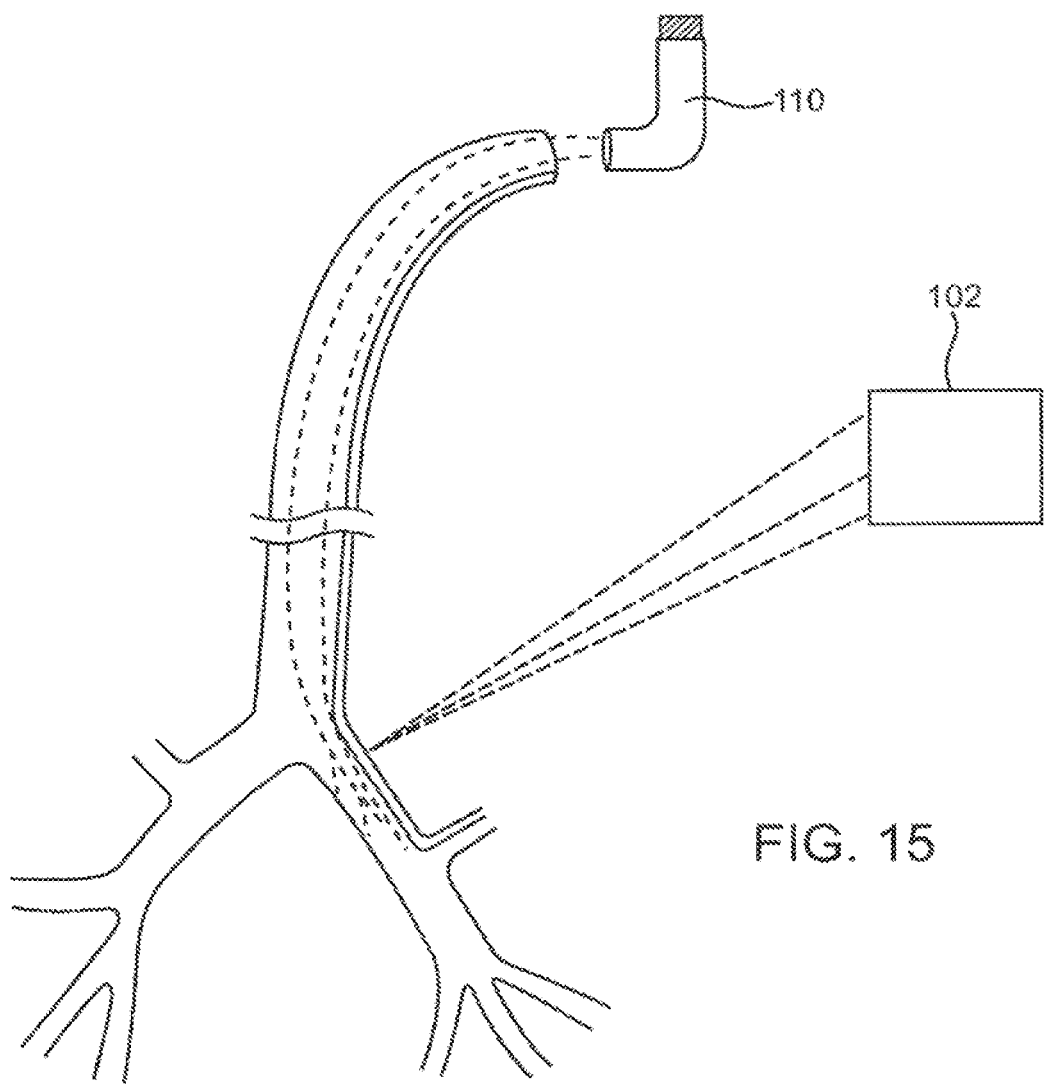
FIG. 15—depicts a method of use of a noninvasive agent delivery device coupled with a non-invasive energy source for treating a lumen or tract of the respiratory system.

A combination of these non-invasive approaches may also be advantageous as shown in FIG. 15, wherein an non-invasive inhaler 110 is used to deliver the BoNT-LC to the target region (such as the lung), and the energy is delivered to the target region by the non-invasive source 102 such as the focused ultrasound (HIFU), stereotactic x-ray, or magnetic resonance transmission as previously described. Due to its non-invasive technique, this approach may have broad appeal to a large patient population, including pediatric use, on an outpatient basis in a clinic designated for the treatment of specific respiratory ailments.

In a further aspect of the present invention, the fragmented molecule BoNT-LC may be delivered intravenously to a patient to achieve a systemic affect. A non-invasive energy application device, such as those described above, may then be targeted at the area of interest to porate the target area, thereby locally delivering the BoNT-LC to the region sufficiently porated by the applied energy.

Figure 14:
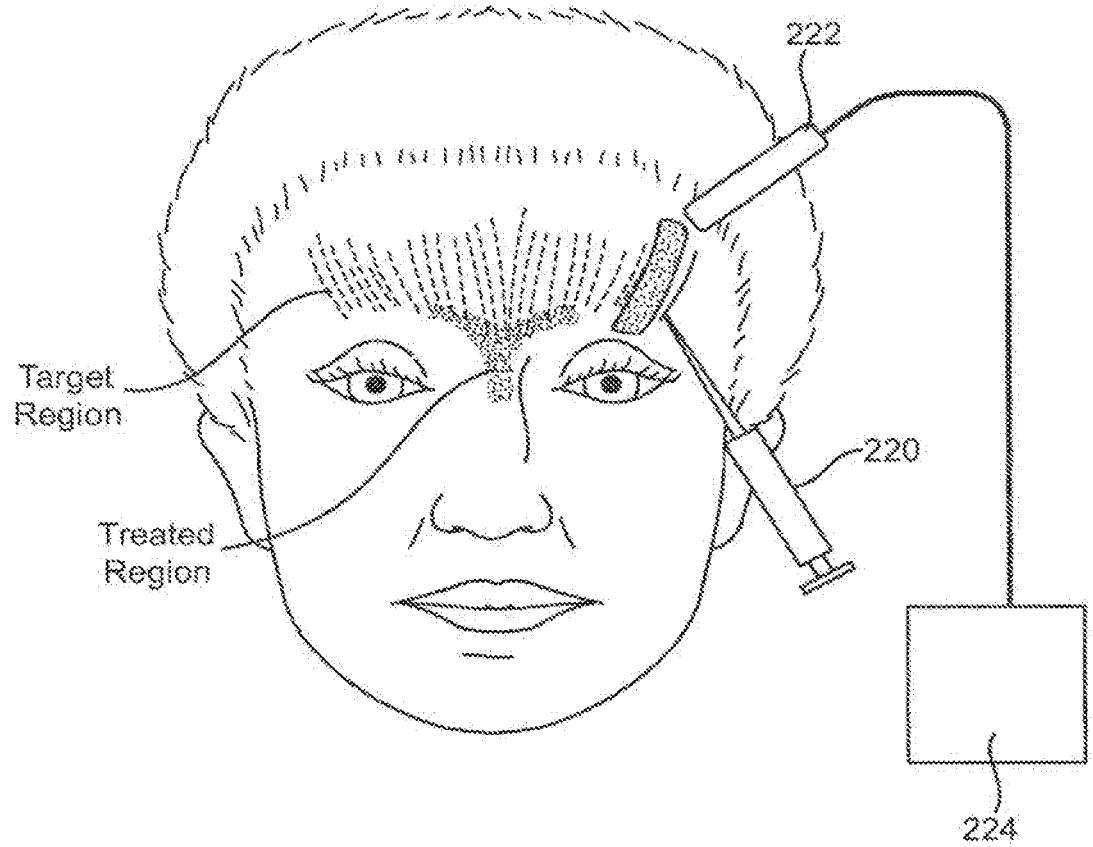
FIG. 14—depicts an embodiment of the present invention wherein the energy and therapeutic agent are delivered transdermally.

Cosmetic and Myofacial Applications. For some conditions, it may be desirable to apply the energy field from the surface of the skin to produce a porative effect, while injecting the BoNT-LC fragment into the targeted facial muscles as shown in FIG. 14. In operation, an injection device 220 places the BoNT-LC in the muscle to be treated (target region), and an energy transmission device such as an ultrasonic pen 222 with a single, or a series of ultrasonic elements located on the distal end and coupled to an energy transmission system 224, follows along the target region to controllably discharge the BoNT-LC fragments to the targeted cells leaving a highly controlled treated region. In some instances for treatments around the eye, it may be desirable to limit the penetration of the BoNT-LC to dermal or subdermal layers. In these applications, BoNT-LC may be applied transdermally with ultrasound assistance using techniques similar to those set forth in U.S. Pat. No. 4,767,402 to Kost the contents of which is expressly incorporated herein in its entirety or through transdermal electroporation.

Intraluminal Devices

It may further be advantageous to position catheters of the present invention through vessels in the body to direct them to various regions to affect neurotransmitters in the cardiovascular system. Intraluminal catheters such as those shown in United States Patent Applications 2001/0044596 to Jaafar and 2002/0198512 to Seward, hereby incorporated by reference in their entirety, may be used in this application of the present invention.

Treatment Enhancements

In some applications of the present invention, it may be desirable to assess the appropriate location for the therapy prior to treatment, the therapeutic effect as it is delivered, and ultimately the resulting effect. To achieve this, once the treatment device is in place adjacent the tissue to be treated, the energy generator may be activated, causing an energized field to be generated in the target area. Prior to activation of therapeutic voltages and agent, stimulation using one or more electrodes may be used to elicit a nerve response or reflex. By observing the nerve response, a target treatment location can be confirmed. Similarly, once the therapy has been delivered, a similar stimulation response may be sought, to determine presence or lack of neurogenic response.

In operation, effects of electroporation and delivery of a therapeutic dose of BoNT LC may be selective due to the cellular structure and orientation of the targeted cells. For example, targeted cells may be preferentially affected due to size, avoiding smaller or cross-oriented tissue cells.

In a further aspect of the present invention, the method of delivering the LC fragment of the BoNT molecule may include the use of a media that contains microspheres or microbubbles, such as Optison™ sold by GE Healthcare (www.amershamhealth-us.com/optison/). Delivery of an ultrasound energy (or other form of energy, for example, laser, RF, thermal, energy) to the media causes the microspheres to rupture, which causes a release of energy toward the targeted region. Such a technique may assist in the desired porative effect by reducing the amount of applied energy required to create poration in the targeted cell membrane. *Bioeffects Caused by Changes in Acoustic Cavitation Bubble Density and Cell Concentration: A Unified Explanation Based on Cell-to-Bubble Ratio and Blast Radius*, Guzman, et al. Ultrasound in Med. & Biol., Vol. 29, No. 8, pp. 1211-1222 (2003). In an alternative embodiment, the LC fragment may actually be contained or encapsulated within a microsphere to assist in delivery. Such enhancing elements may be delivered prior to energy application or during energy application.

In a further aspect of the present invention, it may be advantageous to heat the targeted cells or surrounding tissue by either applying thermal energy directly to the region, or directing a heated fluid, such as saline to the region through an injection element, to aid the cell poration process. Other substances may also be injected to aid in the transmission of the BoNT-LC into the intracellular membrane, such as amino acids, detergents or other agents that may facilitate the catalytic activity of the LC, in addition to the applied energy.

Figure 15A:
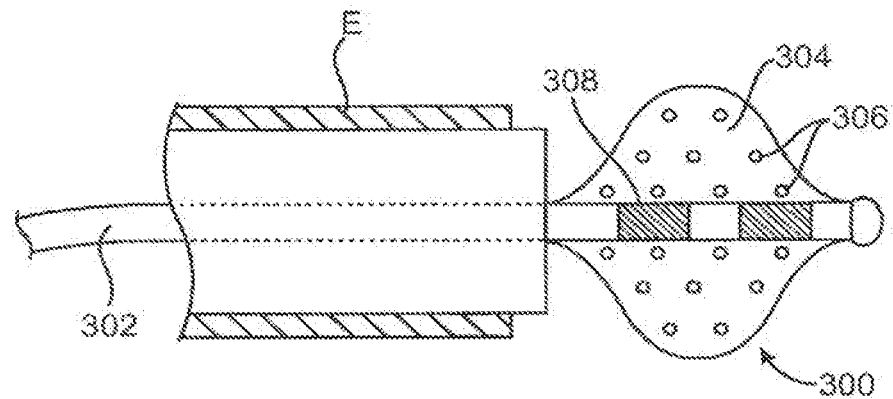
FIGS. 15A and 15B—depict use of a balloon for delivering toxin fragments in a lung.
Figure 15B:
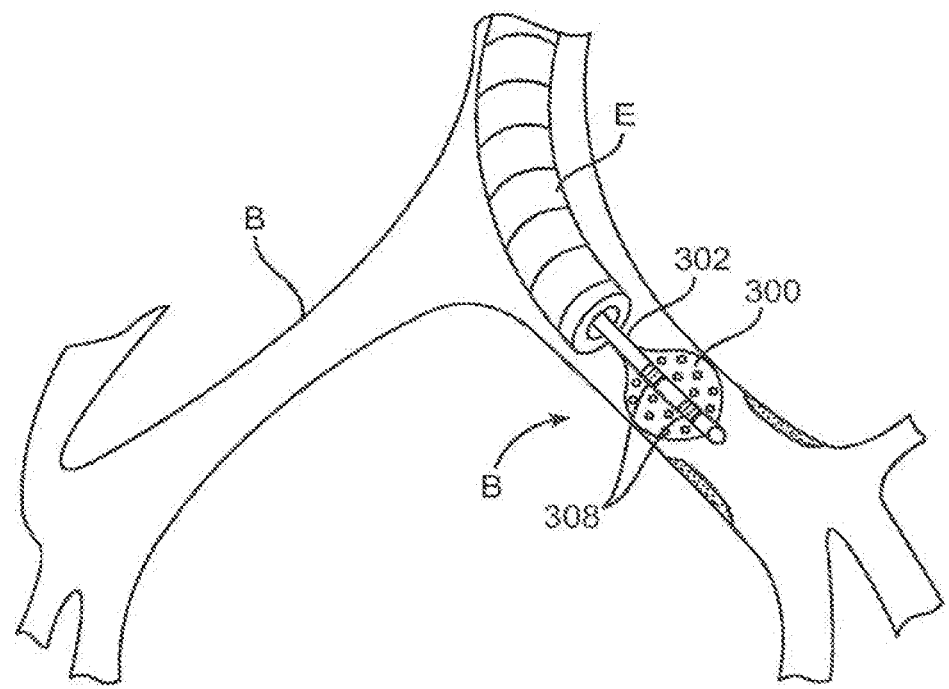

Referring now to FIGS. 15A and 15B, a balloon catheter 300 may be delivered to a target site in the bronchus B of a lung (FIG. 15B). Typically, the catheter 300 will be delivered through an endoscope E, and the shaft 302 of the catheter will comprise at least one lumen for inflating the balloon 304. The inflation medium may carry the toxin fragment which is released through ports 306 formed in the balloon itself. Thus, inflation of the balloon both engages the ports against the wall of the bronchus B and provides the pressure necessary to infuse the neurotoxin fragments into the wall of the bronchus B. Usually, energy will be applied from electrodes 308 or other transducers located within the balloon 304.

Figure 16A:
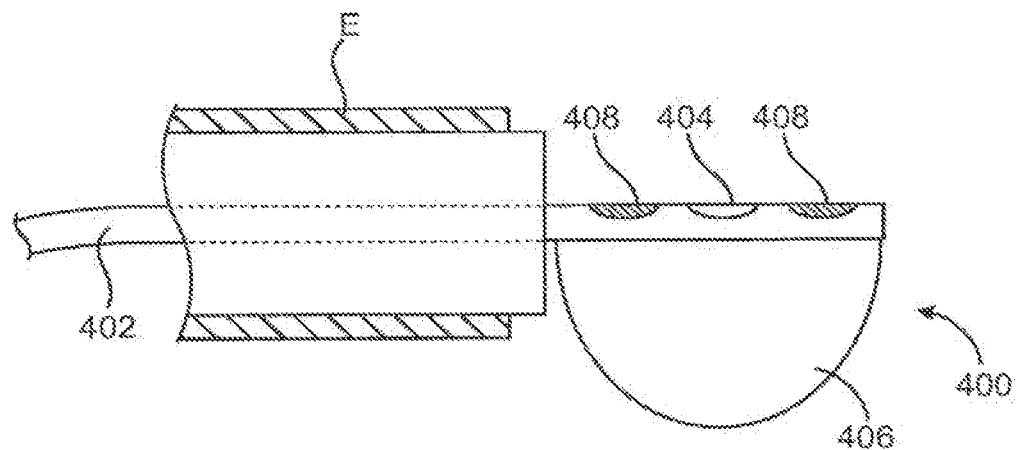
FIGS. 16A and 16B—depict use of a deflected catheter tip for delivering toxin fragments in a lung.
Figure 16B:
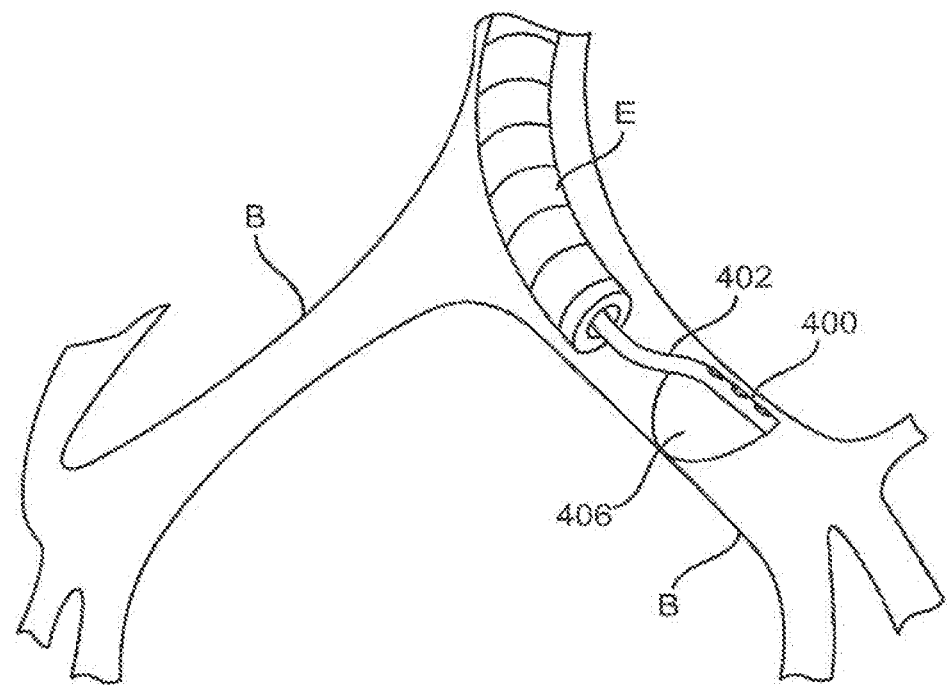

Referring now FIGS. 16A and 16B, the catheter 400 may also be delivered to a bronchus B of a lung through an endoscope E. Catheter shaft 402 terminates with a delivery port 404 near its distal end. A deflection balloon 406 (or other expandable element capable of pressing against the wall of the bronchus B to engage the port 404 against target tissue) is provided on a side of the catheter shaft 402 which is opposite to that of the port 404. Electrodes 408 are provided on either side of the port 404 in order to deliver the poration energy into the target tissue.

Although various illustrative embodiments of the present invention are described above, it will be evident to one skilled in the art that various changes and modifications may be made without departing from the scope of the invention. It will also be apparent that various changes and modifications may be made herein without departing from the invention. The appended claims are intended to cover all such changes and modifications that fall within the true spirit and scope of the invention.

What is claimed is:

1. A nerve modification device for altering nerve function in a bronchial airway of a patient, the nerve modification device comprising:
   a main catheter body configured to extend through a trachea into the bronchial airway;
   a first electrode coupled to a distal end of the main catheter body, the first electrode being configured to be positioned proximate a target region in an airway wall of the bronchial airway and to emit energy laterally relative to the main catheter body;
   a second electrode configured to be positioned outside of the bronchial airway and remote from the target region; and
   a movable mechanism configured to move the first electrode laterally within the bronchial airway such that the at least one energy emitter contacts a first portion of a circumference of the airway wall,
   wherein the nerve modification device is adapted to produce an energy field between the first electrode and the second electrode and concentrated at the target region in the wall of the bronchial airway in a first lateral direction from the catheter body to alter nerve cells within the target region, and wherein a size and intensity of the energy field is controllable by placement of the first and second electrodes relative to each other and the target region.

2. The nerve modification device of claim 1, wherein the energy is at least one of x-ray energy, radiofrequency energy, DC current, AC current, microwave energy, and ultrasound energy.

3. The nerve modification device of claim 2, wherein the energy is RF energy.

4. The nerve modification device of claim 1, wherein the first electrode comprises at least one ultrasound transducer.

5. The nerve modification device of claim 4, wherein the energy is ultrasound energy.

6. The nerve modification device of claim 1, wherein the movable mechanism comprises an expandable member coupled to the main catheter body, the expandable member being configured to expand to move the first electrode into contact with the first portion of the circumference of the wall.

7. The nerve modification device of claim 6, wherein the expandable member is further configured to expand such that the expandable member engages a second portion of the circumference of the airway wall.

8. The nerve modification device of claim 7, wherein the expandable member is expanded laterally in a second lateral direction from the catheter body opposite the first lateral direction.

9. A system for altering nerve function in a bronchial airway of a patient, the system comprising:
an intraluminal catheter configured to be positioned within a bronchial airway of a patient, the intraluminal catheter including
a main catheter body, and
a first electrode configured to be positioned within the bronchial airway proximate a target region in the airway wall, and to emit energy laterally relative to the main catheter body;
a movable mechanism coupled to a distal end of the main catheter body, and configured to move the first energy emitter laterally within the bronchial airway such that the first energy emitter contacts a first portion of a circumference of the airway wall;
a second electrode configured to be positioned remote from the target region; and
an energy generator operably coupled to the first electrode and configured to activate the first electrode, thereby causing an energy field to be generated the target region in the airway wall to alter nerve cells within the target region, and wherein a size and intensity of the energy field is controllable by placement of the first and second electrodes relative to each other and the target region.

10. The system of claim 9, wherein the second electrode is operably coupled to the energy generator, and coupled to the movable mechanism relative to the first electrode such that an arrangement of the first and second electrodes causes the energy field produced therefrom to be concentrated in a lateral direction from the main catheter body.

11. The system of claim 9, wherein the second electrode is operably coupled to the energy generator, and coupled to the movable mechanism relative to the first electrode such that an arrangement of the first and second electrodes causes the energy field produced therefrom to comprise a uniform energy field about the main catheter body.

12. The system of claim 9, wherein the movable mechanism comprises an expandable member coupled to the mam catheter body, the expandable member being configured to expand to move the first electrode into contact with a first portion of a circumference of the airway wall.

13. The system of claim 12, wherein the expandable member is further configured to expand such that the expandable member engages a second portion of the circumference of the airway wall.

14. The system of claim 9, wherein the energy is at least one of x-ray energy, radiofrequency energy, DC current, AC current, microwave energy, and ultrasound energy.

15. The system of claim 14, wherein the energy is RF energy.

16. The system of claim 9, wherein the second electrode is configured to be positioned outside of the bronchial airway.

* * * * *